United States Patent
Ishikawa et al.

(10) Patent No.: US 6,261,247 B1
(45) Date of Patent: Jul. 17, 2001

(54) POSITION SENSING SYSTEM

(75) Inventors: Akira Ishikawa, Royce City; Nabuo Takeda, Richardson; Suzanne I. Ahn, Dallas, all of TX (US); Samuel S. Ahn, Los Angeles, CA (US); Steven R. Hays, Dallas, TX (US); F. Andrew Gaffney, Nashville, TN (US)

(73) Assignee: Ball Semiconductor, Inc., Allen, TX (US)

( * ) Notice: Subject to any disclaimer, the term of this patent is extended or adjusted under 35 U.S.C. 154(b) by 0 days.

(21) Appl. No.: 09/475,312

(22) Filed: Dec. 30, 1999

Related U.S. Application Data
(60) Provisional application No. 60/114,405, filed on Dec. 31, 1998.

(51) Int. Cl.⁷ .................................................. A61B 5/103
(52) U.S. Cl. ............................. 600/587; 606/1; 33/700; 73/1.79; 600/591
(58) Field of Search .................................... 600/300, 587, 600/591, 595; 342/118; 606/1; 128/897, 898; 33/700; 73/1.79, 490

(56) References Cited

U.S. PATENT DOCUMENTS

| | | | |
|---|---|---|---|
| 3,768,459 | 10/1973 | Cannon et al. | 128/2 S |
| 3,887,916 | * 6/1975 | Goyer | 342/30 |
| 4,245,656 | 1/1981 | Farr et al. | 128/775 |
| 4,249,539 | * 2/1981 | Vilkomerson et al. | 600/461 |
| 4,804,961 | * 2/1989 | Hane | 342/125 |

(List continued on next page.)

FOREIGN PATENT DOCUMENTS

| | | |
|---|---|---|
| 196 31 303 A | 2/1998 | (DE) . |
| 0 567 898 A | 11/1993 | (EP) . |
| 0 242 983 A | 10/1997 | (EP) . |
| WO 84 01688A | 5/1984 | (WO) . |

(List continued on next page.)

OTHER PUBLICATIONS
International Search Report dated Jul. 18, 2000.

*Primary Examiner*—Robert L. Nasser
*Assistant Examiner*—Charles Marmor, II
(74) *Attorney, Agent, or Firm*—Howison, Chauza, Thoma, Handley & Arnott, L.L.P.

(57) ABSTRACT

An anatomical position sensing system (100) using one or more substantially spherical transponders for measuring relative positions and distances. Transponders (P) and (S) are capable of receiving and transmitting RF signals, and communicating between themselves and with a separate CPU (112). The CPU (112) is controlled by an operator at an operator control panel (114), interacts with an alarm (120) for providing audible alerts to the operator, and a display for displaying information to the operator. The CPU (112) controls a broadband antenna (118) to transmit, at a frequency $f_1$, a low-frequency RF power signal (122) across a wide field to energize the transponders (P) and (S). Directional components (122a) and (122b) intercept and energize the transponders (P) and (S). Once energized, transponder (P) transmits a range signal in all directions including component (124) at a very high RF frequency $f_2$, extending from transponder (P) to transponder (S). Upon receipt of the range signal (124), transponder (S) emits a data signal at a very high RF frequency $f_3$ in all directions, including component (126), which is directed at the antenna (118). The distance (D) is determined by measuring the attenuation of the range signal (124) as it is received by transponder (S). Transponder (S) then modulates the value of the strength of the incoming range signal (124) onto the data signal. The CPU (112) computes the distance (D) from the incoming data signal (126) from a lookup table derived from a sequence of calibration steps prior to beginning normal operation.

50 Claims, 15 Drawing Sheets

U.S. PATENT DOCUMENTS

| | | | |
|---|---|---|---|
| 5,202,684 | * 4/1993 | Funatsu | 340/961 |
| 5,415,864 | 5/1995 | Kopecek et al. | 424/436 |
| 5,469,861 | 11/1995 | Piscopo et al. | 128/781 |
| 5,826,578 | * 10/1998 | Curchod | 600/595 |
| 5,833,603 | * 11/1998 | Kovacs et al. | 600/317 |
| 5,887,176 | * 3/1999 | Griffith et al. | 713/320 |
| 6,067,039 | * 5/2000 | Pyner et al. | 342/125 |

FOREIGN PATENT DOCUMENTS

| | | | |
|---|---|---|---|
| WO 98/25090 | 6/1998 | (WO) | F27B/15/00 |
| WO 99/55360 | 11/1999 | (WO) | A61K/38/17 |
| WO 00/15140 A | 3/2000 | (WO) | A61F/2/00 |
| WO 00/38571 | 7/2000 | (WO) | A61B/5/00 |

* cited by examiner

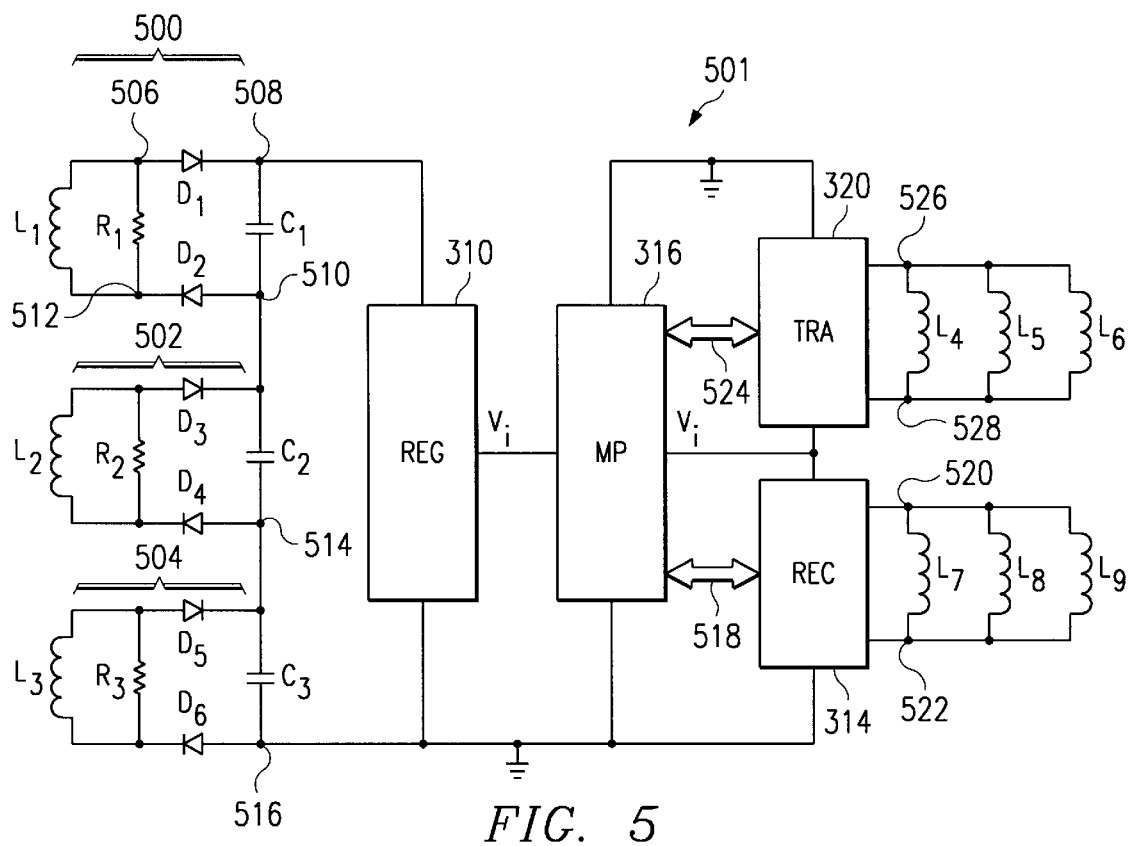
FIG. 5
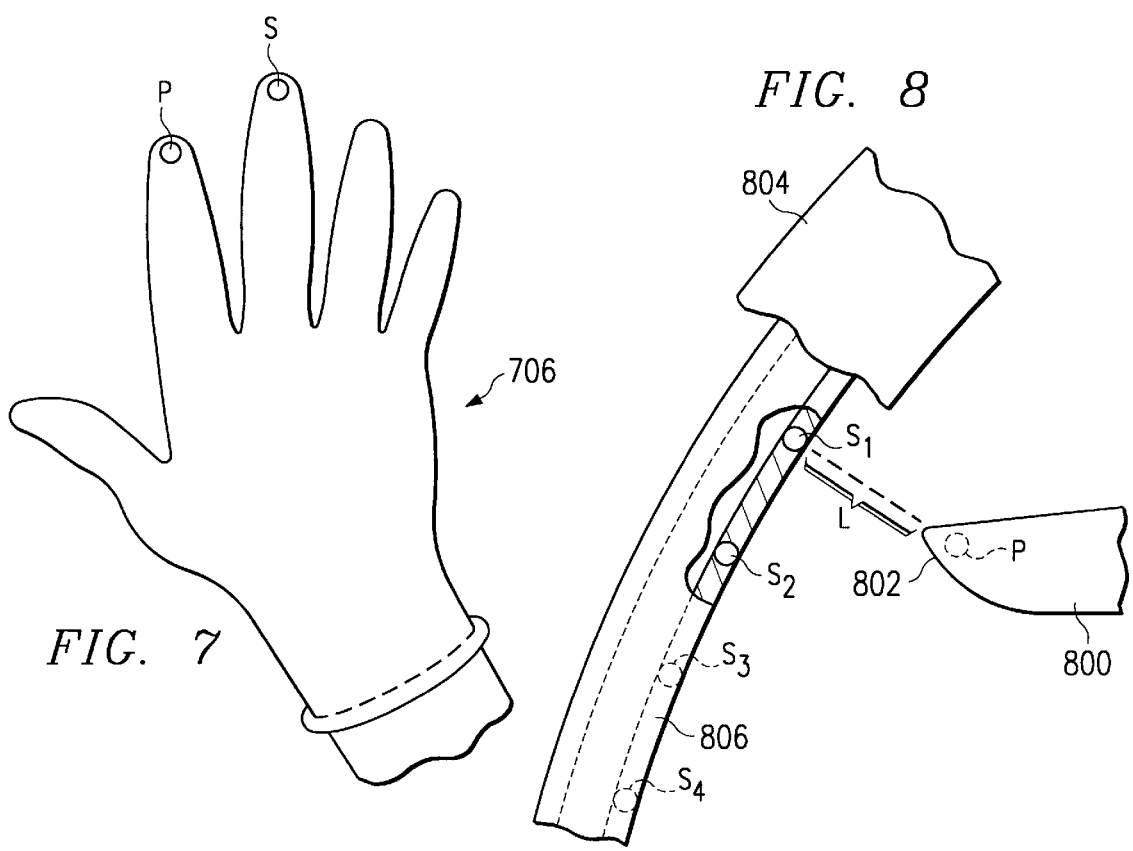
FIG. 7
FIG. 8

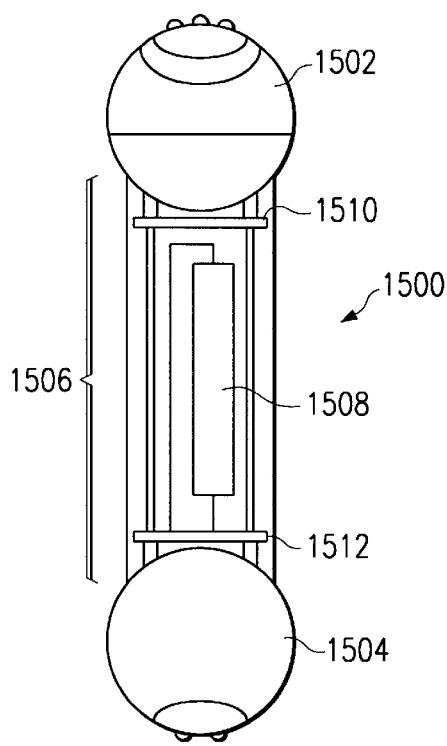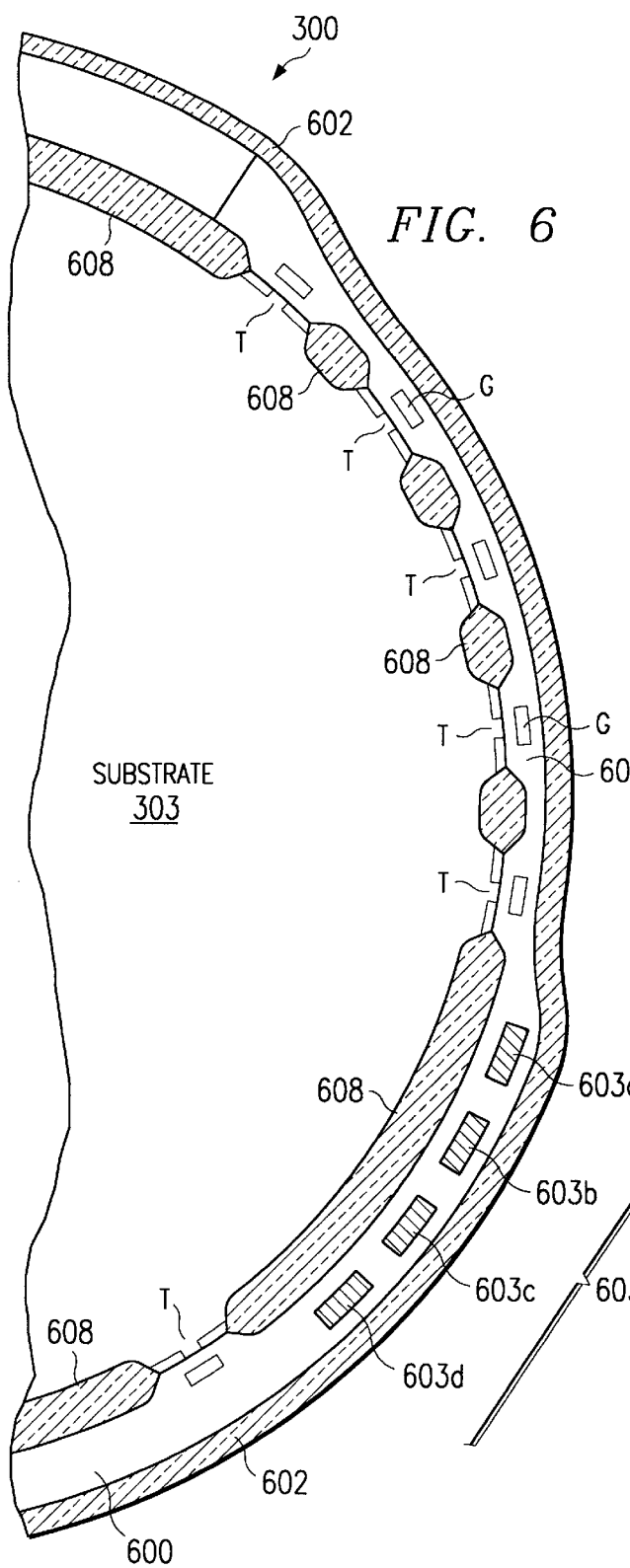

POSITION SENSING SYSTEM

CROSS-REFERENCE TO RELATED APPLICATIONS

This application claims priority under 35 U.S.C. 119(e) from U.S. Provisional Patent Application Serial No. 60/114,405 filed on Dec. 31, 1998, having the same title as this application.

This application is related to the following commonly assigned co-pending U.S. Patent applications: Ser. No. 09/448,642 entitled "Miniature Spherical-Shaped Semiconductor With Transducer;" Ser. No. 09/448,641 entitled "Intraluminal Monitoring System;" Ser. No. 09/448,781 entitled "Spherical-Shaped Biomedical IC;" Ser. No. 09/448,678 entitled "Method of and System for Identifying Medical Products;" Ser. No. 09/448,638 entitled "Internal Thermometer;" and Ser. No. 09/448,644 entitled "Monitor for Interventional Procedures;" each of which were filed on Nov. 24, 1999, and co-pending U.S. patent application Ser. No. 09/475,819 entitled "Injectable Thermal Balls For Tumor Ablation," filed of even date with this application, and each of which is incorporated herein by reference.

TECHNICAL FIELD OF THE INVENTION

The present invention relates to electronic distance measurement, and more particularly to miniature electronic devices and systems for monitoring relative anatomic positions and locations.

BACKGROUND OF THE INVENTION

Precise knowledge of a patient's anatomical structures is a basic requirement for effective and correct diagnosis and treatment of diseases. However, human anatomy varies considerably from patient to patient, and the relative positions of anatomic structures can be altered by injury, disease processes (displacement by tumor or inflammation), and previous operations. Conventional imaging techniques used to determine the positions of anatomical structures include computerized axial tomography scanning and magnetic resonance imaging which are excellent for anatomic localization, but the techniques are only available using machines which are large and expensive, and consequently, require special facilities for use and operation. Further, these machines are not readily available at the bedside of the patient or in the operating room. Therefore, a more desirable alternative is needed whereby the position of anatomical structures can be more readily ascertained without the use of these expensive and cumbersome machines.

Pregnant women routinely undergo pelvic examinations during labor and delivery to monitor certain parameters that are important for a successful birth of the child and survival of the mother. A pelvis that is too small to allow delivery of the fetus can lead to complications during delivery, including loss of the fetus and, in some cases, complications leading to loss of life of the mother. One method for determining the size of the pelvis is based on guesswork and experience where palpation of the pelvic bone is performed using the index and middle fingers. Other methods are pelvimetry which is performed by x-ray which may contain potentially harmful radiation, or by ultrasound which is somewhat cumbersome and expensive.

Another preparatory procedure during labor and delivery is the repeated manual examination of the dimensions of the cervix during its progressive dilation to allow passage of the fetus. Current measurements are done digitally using the index and middle fingers. This repeated examination increases the incidence of infection in the fetus and mother. Therefore, a less invasive procedure is desirable to reduce the risk of infection and to more accurately track the size of the cervix during the birthing process.

When surgery is required, the potential for complications is heightened by the inadvertent damage to veins, arteries, and ducts. Surgery can be particularly hazardous when there is inflammation due to infections, scar tissue, fibrosis due to previous surgery, or distortion of anatomy due to tumors. For example, the pelvis contains the ureter, and the iliac artery and vein in close proximity to the other pelvic organs such as the uterus, ovaries, intestines, and bladder, which often require surgical treatments. In the presence of inflammation and scar tissue, surgery in this area can be quite hazardous because of the potential injury to the ureter, and the iliac artery and vein which can be encased and distorted. Similarly, the structures of the biliary system, consisting of the gallbladder, the common bile duct, and the portal vein, often become inflamed secondary to obstruction and infection, and surgical resection of the gallbladder and/or exploration of the common bile duct are necessary to treat such disease processes. During such surgery, injury to the common bile duct and the adjacent portal vein occurs too frequently. Such complications can be disastrous to the patient. Therefore, a method of accurately determining the position of veins, arteries, and ducts in relation to the cutting instrument is crucial during surgery in order reduce the potential for hazardous or even fatal complications due to the damage of these vital structures.

The position sensors may also be used to detect movement or displacement of structures. For example, position sensors can be positioned over the ribs or intercostal muscles to detect movement during respiration. In addition, position sensors can be temporarily affixed to bone intraoperatively to allow correct positioning of artificial limbs or joints. Current methodology for alignment of hip joints requires manual and visual means leading to malalignment, a major cause of morbidity in patients undergoing this procedure.

Position sensors and accelerometers are vital components for stereotactic surgery instruments utilized in neurologic, ophthalomoligic, orthopedic, and laparoscopic surgeries. The disclosed sensors allow for precise positioning and guidance of surgical instruments in critical areas. The miniature size of the ball position sensor allows for smaller instrumentation and less damage to vital structures.

SUMMARY OF THE INVENTION

The invention disclosed and claimed herein is a system for sensing relative positions. The system comprises a processing unit for processing information; and at least first and second substantially spherical transponders in communication with the processing unit and having a distance therebetween, which the distance is determinable with the processing unit.

BRIEF DESCRIPTION OF THE DRAWINGS

For a more complete understanding of the present invention and the advantages thereof, reference is now made to the following description taken in conjunction with the accompanying Drawings in which:

FIG. 5 illustrates a circuit architecture for implementing the transponder functions;

FIG. 6 illustrates additional details of the semiconductor structure of the transponder;

FIG. 7 illustrates an alternative embodiment where transponders are used in the fingertips of surgical gloves;

FIG. 8 illustrates an alternative embodiment where a transponder is used as a proximity warning device during surgery;

FIG. 15 illustrates a side view of an alternative embodiment of a transponder utilized in conjunction with a stimulus function;

DETAILED DESCRIPTION OF THE INVENTION

The transponder ball disclosed herein offers a number of advantages over conventional semiconductor devices having a planar or two-dimensional geometry. By way of illustration, a few of these advantages include the following: a spherical device has a smooth, rounded shape which is easily implanted or injected into a biological medium and which passes easily through a biological medium, if necessary in a particular application. Further, the large surface area of a spherical device relative to its overall dimensions provides for the maximum of surface area devoted to functional regions in contact with the biological medium, such as transducers and other circuitry. Further, the spherical device permits the disposition of onboard semiconductor devices to be aligned on all three geometric axes for maximum function on a single substrate.

Figure 1:
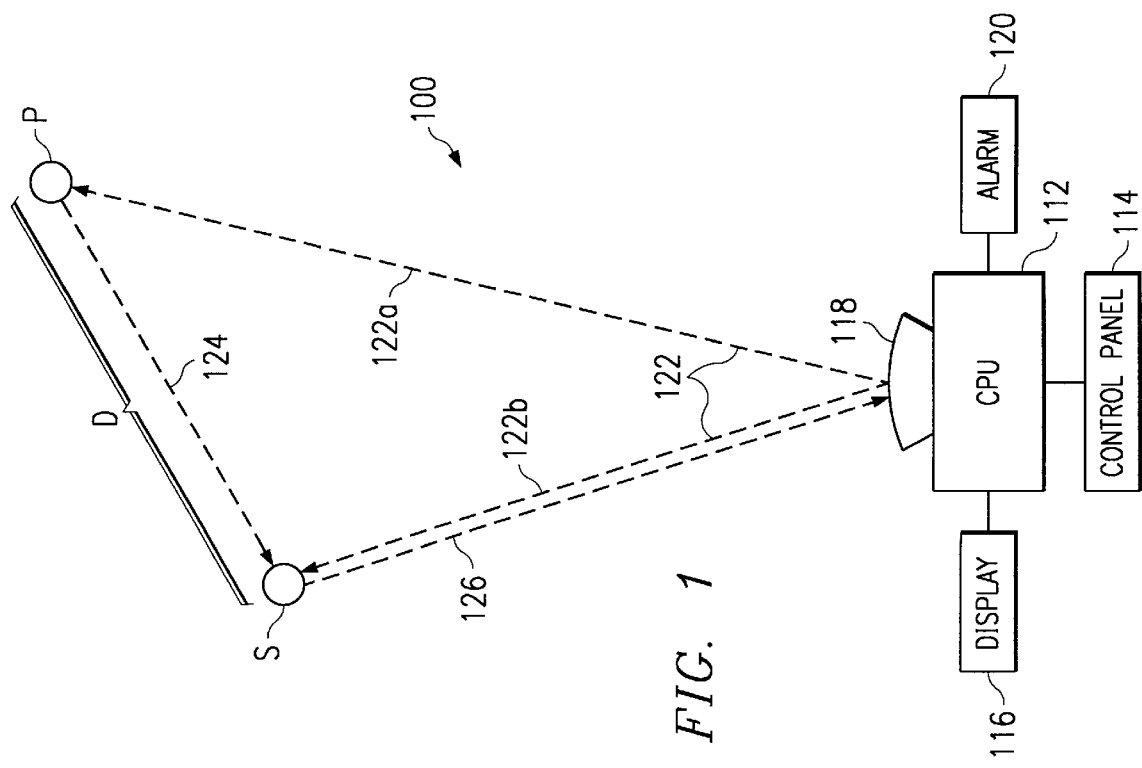
FIG. 1 illustrates a system for measuring the distance between two points, such as two anatomical structures, according to a disclosed embodiment.

Referring now to FIG. 1, there is illustrated a system for measuring the distance between two points, such as two anatomical structures. A system 100 includes a primary transponder P and a secondary transponder S, which are separated by a distance D. The transponders P and S preferably are spherical-shaped semiconductor devices or "balls" that are fabricated using techniques described in a commonly-assigned U.S. Pat. No. 5,955,776 entitled "Spherical Shaped Semiconductor Integrated Circuit," which issued Sep. 21, 1999, and which is herein incorporated by reference. An integrated circuit (IC) can be provided on such semiconductor balls to enable them to perform relatively complex tasks considering their small size, which may be one millimeter in diameter or smaller.

Transponders P and S are capable of receiving and transmitting radio frequency (RF) signals and communicating between themselves and with a separate central processing unit (CPU) 112. The CPU 112 is controlled by an operator by means of a control panel 114, which may include specialized dials and/or a conventional keyboard for entering parameters into a memory within the CPU 112. The CPU 112 communicates with the operator through a display 116, which may be a conventional computer CRT screen. The CPU 112 includes a broadband antenna 118 for transmitting and receiving RF signals. Also, the CPU 112 preferably selectively activates an audible alarm 120, such as a beeper, for alerting the operator upon the occurrence of a particular condition.

In operation, the system 100 determines the distance D between the primary transponder P and the secondary transponder S using RF signals. Preferably, the transponders P and S are passive so as to eliminate the need for batteries and the space requirements associated therewith. Thus, the transponders P and S can be employed in applications in which a very small size is an advantage or a necessity. Many medical applications for the inventive system 100 are possible, some of which are described hereinbelow. To energize the transponders P and S, a low frequency RF signal or power signal 122 is transmitted at a first frequency $f_1$ by the CPU 112. The power signal 122 is sent out from the antenna 118 across a wide field which includes directional components 122a and 122b. Once energized, the transponders P and S begin operation, each according to its own internally stored instructions or instructions transmitted thereto. Transponder P transmits a range signal in all directions including component 124 from transponder P at a very high RF frequency $f_2$, as indicated by the dashed line extending from transponder P to transponder S. Upon receipt of the range signal 124 by the transponder S, the transponder S emits a data signal at a very high RF frequency $f_3$ in all directions, including component 126, which is directed at the antenna 118.

Preferably, the distance D is determined by measuring the attenuation of the range signal 124 as it is received by transponder S. The range signal 124 is transmitted from transponder P at a known amplitude or signal strength. The attenuation in the signal strength is a function of the distance D from the transponder P. The attenuation drops off as the square of the distance D, allowing a relatively precise measurement of D from the signal strength as received by transponder S. Transponder S then modulates the value of the strength of the incoming range signal 124 onto the data signal. The CPU 112 computes the distance D from the incoming data signal 126 using a lookup table developed from a sequence of calibration steps prior to beginning normal operation. The calibration steps can be accomplished by measuring D for various separation distances throughout the operable range, which may be about several meters. Subsequently, when the distance D is not known, the CPU 112 can calculate the distance D from the incoming data signal 126. The resulting distance can be output to the display 116. If the distance is less than some predetermined value set by the control panel 114, the CPU 112 can generate an alarm, such as a series of rapid beeps, using the audible alarm 120. The system 100 is intended primarily for application in measuring separation distances of a fraction of a meter, such as ten centimeters or less, to an accuracy within about two millimeters.

Figure 2:
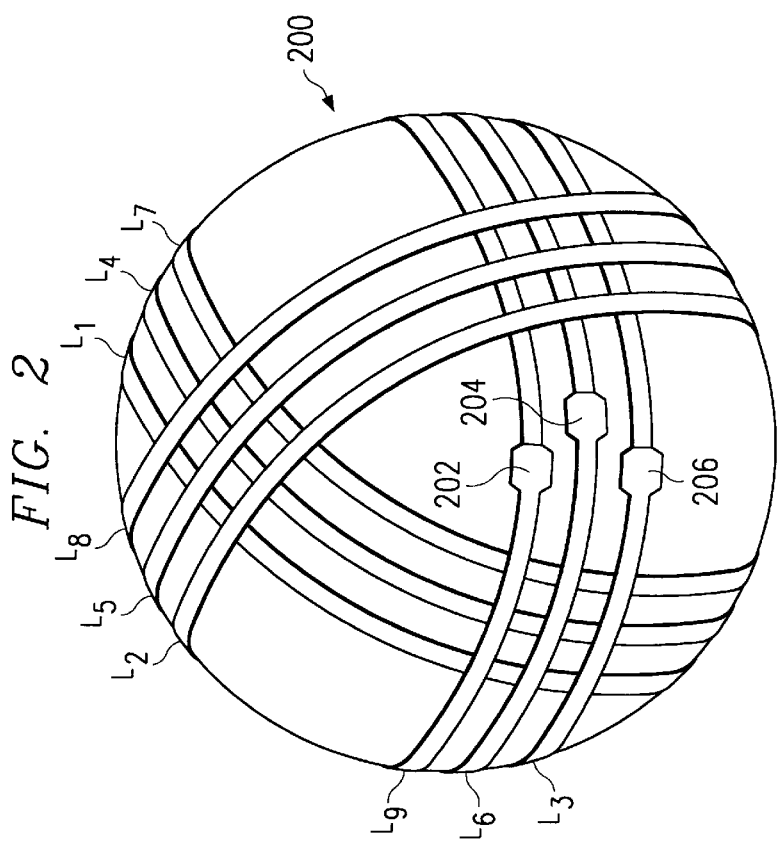
FIG. 2 illustrates an implementation of one or more inductive coils of a transponder ball.

Referring now to FIG. 2, there is illustrated an implementation of one or more inductive coils of a transponder ball 200. Coils $L_1$, $L_4$ and $L_7$ are arranged in parallel planes that are perpendicular to a first axis; coils $L_2$, $L_5$ and $L_8$ are arranged in parallel planes that are perpendicular to a second axis; and coils $L_3$, $L_6$ and $L_9$ are arranged in parallel planes that are perpendicular to a third axis. The first, second and third axes are mutually perpendicular. Each of the inductive coils $L_1$–$L_9$ includes multiple separate windings (not shown). The coils $L_1$–$L_9$ can be formed from successive depositions of metal, such as by a chemical vapor deposition of aluminum. Coils $L_1$, $L_4$ and $L_7$ can be formed from a first metalized layer; coils $L_2$, $L_5$ and $L_8$ can be formed from a second metalized layer insulated from the first metalized layer; and coils $L_3$, $L_6$ and $L_9$ can be formed partially from the first metalized layer and partially from the second metalized layer, and can be connected at overlapping points within pads 202, 204 and 206. Circuit elements (not shown) are formed in underlying layers of conductors, insulators and semiconductor material.

Applications for such transponders are numerous. For example, they can be attached to the tips of a glove worn by a physician during nonvisible examination of a patient (pelvic examination or intra-abdominal exploration during abdominal surgery). The miniature transponders may also be attached to a catheter or guidewire placed inside of a vascular or luminal (ureter) structure, and upon surgical scalpels, needles, and scissors. The distance between the transponders located on the scalpel and inside the vessel on the catheter can be monitored to prevent accidental surgical harm to catheterized or tagged vital structures. The transponder balls include sensors and circuitry for transmitting information to an external processing unit for display or to produce an auditory warning. In addition, position sensing transponders can be attached to prosthetic devices to detect angle of movements of a prosthetic joint. Following artificial knee and shoulder replacement, increasing ranges of motion of the prosthetic joint are required for continued rehabilitation. Alternatively, following artificial hip replacement surgery, the range of the hip joint motion needs to be initially limited to improve long term hip function. Ball transponders attached to the artificial prosthetic devices and surrounding bone can be used to monitor the joint range of motion. Furthermore, transponders can be located near the end of microscopic surgical instruments where stereotactic surgical precision is required.

Figure 3:
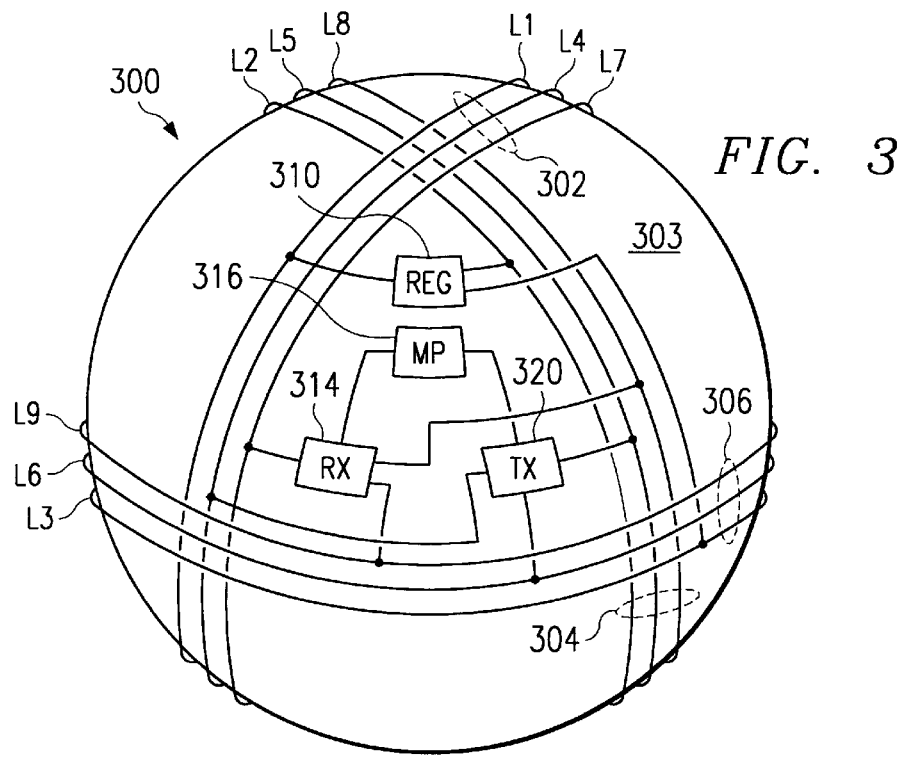
FIG. 3 illustrates spherical geometry of a transponder according to a disclosed embodiment.

Referring now to FIG. 3, there is illustrated spherical geometry of a transponder 300, according to a disclosed embodiment. The transponder 300 (similar to transponder 200) is fabricated on a substantially spherical substrate 303, and includes nine coils $L_1$–$L_9$ in three sets 302, 304, and 306 of three coils, each set 302, 304, and 306 preferably orthogonal to each other so that power and signal communication requirements can be optimized according to the orientation of each transponder ball 300. Each coil set 302, 304, and 306 comprises three coils; one transmit coil, one receive coil, and a power coupling coil. Therefore, in this embodiment, there are three power coils $L_1$, $L_2$, and $L_3$; three transmit coils $L_4$, $L_5$, and $L_6$; and three receive coils $L_7$, $L_8$, and $L_9$. The coils sets are grouped in this fashion to ensure that at least one coil set is orientated to provide potentially optimum power coupling and signal communication therewith. Onboard circuitry comprises a processor circuit 316 for controlling all aspects of the transponder ball 300. The processor circuit can be a digital signal processor or other conventional processor. Power for the transponder 300 is provided via a regulator circuit 310 which regulates power coupled into any of the power coils $L_1$, $L_2$, and $L_3$. Communications are provided by a transmit circuit 320 and a receive circuit 314. The transmit circuit 320 connects to the three transmit coils $L_4$, $L_5$, and $L_6$ in order to provide transmit communications which are capable of outputting signals in any orientation of the transponder 300, and only one of which is included in one of the three sets of coils 302, 304, and 306. Similarly, the receive circuit 314 connects to each of the receive coils $L_7$, $L_8$, and $L_9$, in order to provide receive communications which are capable of receiving signals in any orientation of the transponder 300, and only one of which is included in each one of the three sets of coils 302, 304, and 306. The coils $L_1$–$L_9$ can have any number of windings (not shown) in order to achieve the desired results.

The coils $L_1$–$L_9$ are connected by subsurface conductors (not shown) to the other circuit elements on the transponder 300. The processor 316 provides an output to the transmitter 320 that preferably radiates an RF signal to the external antenna 118 for processing by the CPU 112. The power regulator 310 provides a relatively constant DC voltage of about 3.0 volts to the circuits on the transponder 300. A disclosed power source for the transponder 300 is provided by the CPU 112 in conjunction with the antenna 118 which couples power to the power coils $L_1$, $L_2$, and $L_3$ in the form of a varying magnetic field. Alternatively, the transponder 300 can be powered by a miniature battery connected to the transponder 300 (which is discussed in greater detail hereinbelow). The miniature battery can also be in the shape of a ball (battery ball) configured to accommodate a common connection scheme for use between adjacent balls. Preferably, battery balls can be fashioned as electrical double-layer condensers from such materials as manganese dioxide, lithium or lithium ion, samarium-cobalt, carbon, etc. Since such a battery ball is a greater capacity energy source than an RF energy receiving coil, longer communication distances can be achieved by this means. Both the external magnetic field generator (CPU system 112) and receiver antenna 118 can be included in the same computer-controlled apparatus or CPU station within proximity of the transponder 300, at least, but not limited to periods when its operation is required.

Figure 4:
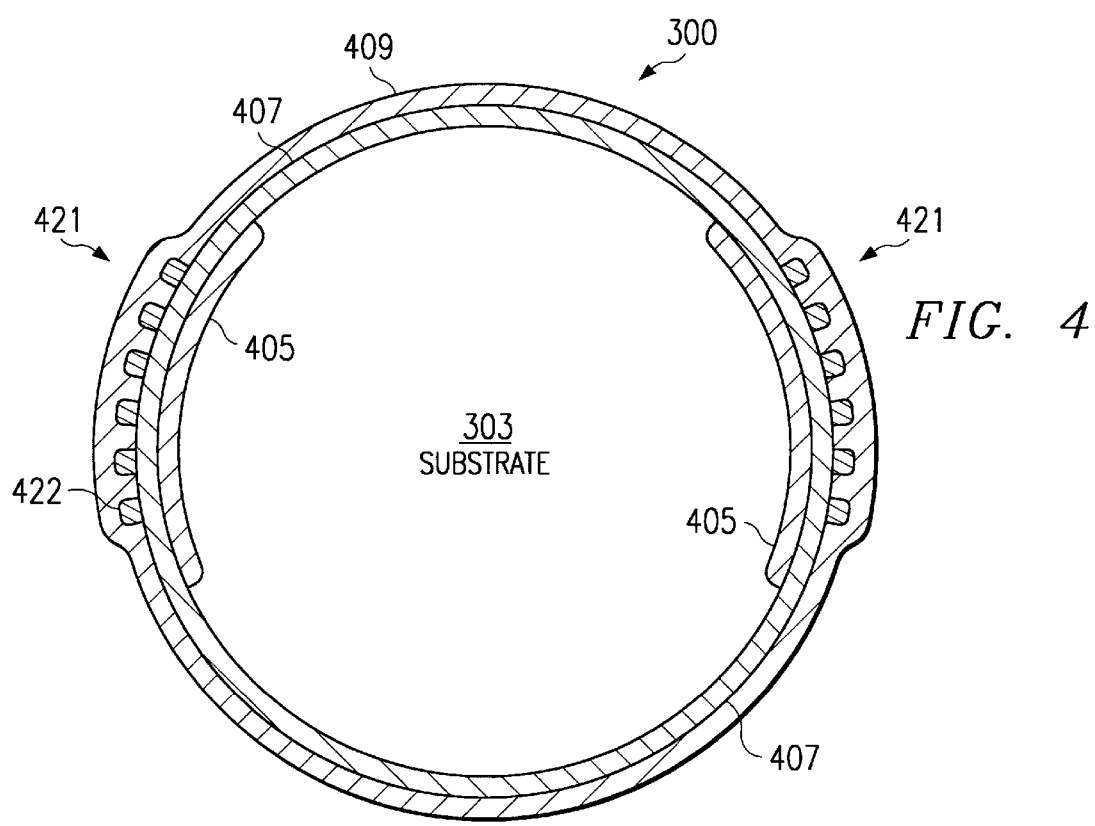
FIG. 4 illustrates a cross section of a transponder ball, preferably comprising a spherical-shaped semiconductor device on which an integrated circuit has been formed.

Referring now to FIG. 4, there is illustrated a cross section of a transponder ball, preferably comprising a spherical-shaped semiconductor device on which an integrated circuit has been formed. Such a spherical-shaped integrated circuit semiconductor device (sometimes referred to herein as a "ball") is described in, commonly assigned, U.S. Pat. No. 5,955,776, issued Sep. 21, 1999, and entitled "Spherical Shaped Semiconductor Integrated Circuit," the disclosure of which is referenced hereinabove. Transponder 300 is built on the substantially spherical semiconductor substrate 303, which may be doped P-type or N-type in accordance with the particular requirements of the fabrication process. Semiconductor circuitry indicated generally at 405 resides on the substrate 303. Circuitry 405 includes the elements illustrated in FIG. 3, including the power regulator 310, the transmit and receive circuits 314 and 320, the processor 316, as well as other circuitry. The substrate 303 and circuitry 405 are covered with an insulating layer 407 which is preferably formed of silicon dioxide or phosphosilicate glass (PSG). A power coil 421 (one of $L_1$, $L_2$, and $L_3$), described with respect to FIG. 3, is formed of helically wrapped windings over the insulating shell 407. The power coil 421 may be fabricated from a deposited layer of aluminum (or copper, gold, etc.) that is patterned and etched using conventional semiconductor fabrication techniques. The actual number of individual windings 422 of power coil 421 may be more or less than the six shown in FIG. 4.

The transponder 300 is coated with or encapsulated in a coating layer 409 of a biological inert material such as phosphosilicate glass. The coating 409 is inert and can withstand potential chemical degradation into which it contacts, for example, the acidity of the stomach, to a very low pH level, and it is not subject to the enzymatic actions of the digestive tract. Transponder 300 is substantially spherical and preferably about one millimeter in diameter. The very small size of transponder 300 enables it to be embedded in surgical or medical tools and apparatus.

Referring now to FIG. 5, there is illustrated a circuit architecture for implementing the transponder functions. Transponders P and S have specific functional differences that may be determined by different sets of stored of instructions. The common circuit architecture for transponders P and S (similar to transponder 300) is indicated generally by reference numeral 501. The onboard circuit 501 comprises three power coil circuits 500, 502, and 504, and respective power coils $L_1$, $L_2$, and $L_3$. Each power circuit 500, 502, and 504 comprises as its basic elements, a resistor in parallel with the power coil, rectifying diodes, and a storage/smoothing capacitor. For example, power circuit 500 comprises a power coil $L_1$ with a parallel resistor $R_1$, rectifying diodes $D_1$ and $D_2$, and capacitor $C_1$ to provide storage, smoothing, and a stable voltage level for the signal entering the regulator circuit 310. The anode of diode $D_1$ connects to a node 506 common to one side of a leg of both the resistor $R_1$ and the coil $L_1$. The cathode of the diode $D_1$ connects to a node 508 which is the upper plate of the capacitor $C_1$, which is also the high-side input of the regulator 310.

The other plate of the capacitor $C_1$ connects to a node 510, which is the anode of diode $D_2$, and the node common to the high-side output of power circuit 502, which is the upper plate of capacitor $C_2$. The cathode of diode $D_2$ connects to a node 512 which is common to the other ends of the resistor $R_1$ and the power coil $L_1$. When the currents induced in the coils $L_1$, $L_2$ and $L_3$ are in the directions blocked by the diodes, the currents are dissipated in resistors $R_1$, $R_2$ and $R_3$. The circuit is tuned to a frequency $f_1$ dependent upon the $R_1C_1$ values. Therefore, where this circuit utilizes three power circuits 500, 502, and 504, there will be provided power coupling at the same frequencies $f_1$, $f_2$, and $f_3$, respectively, provided the RC values are the same. However, it can be appreciated that these resistor and capacitor values could be different such that power is transmitted to the transponder 300 at different frequencies $f_1$, $f_2$, and $f_3$ to provide power coupling operation for all three power circuits.

The second and third power coupling circuits 502 and 504 are structured similarly to the first circuit 500, with the same mix of the resistor, capacitor, and diodes. The second circuit 502 has a power coil $L_2$ with a parallel resistor $R_2$. Diodes $D_3$ and $D_4$ rectify the varying magnetic energy coupled into the coil $L_2$, and capacitor $C_2$ stores the rectified energy, and also smooths the power signal entering the regulator 310 from its leg of the power circuit. The upper plate of capacitor $C_2$ connects to node 510, which is the lower plate of capacitor $C_1$, while the lower plate of capacitor $C_2$ connects to a node 514, which is the upper plate of capacitor $C_3$. Similarly, the third power circuit 504 has a power coil $L_3$ in parallel with a resistor $R_3$. Diodes $D_5$ and $D_6$ rectify the varying magnetic energy coupled into the coil $L_3$, and capacitor $C_3$ stores the rectified energy, and also smooths the power signal entering the regulator 310 from its leg of the power circuit. The lower plate of capacitor $C_3$ connects to the low-side output node 516 of the power regulator 310, which may also be the substrate 303. Power circuits 500, 502, and 504 are connected in series to provide the most power possible to the power regulator 310 in accordance with the power transmitted at the three same or different frequencies $f_1$, $f_2$, and $f_3$, and the particular orientation of the transponder 300 at the time of operation. The resistors $R_2$ and $R_3$ dissipate power when the diodes $D_3$–$D_6$ are in a blocking mode.

The voltage regulator 310 provides a relatively constant voltage $V_i$ that serves as the internal voltage source for other circuit elements of the transponder 300. The output of the power regulator 310 connects to the processor 316 to supply its power needs during operation of the transponder 300.

Similarly, the output voltage of the power regulator 310 is fed to the transmit circuit 320 and the receive circuit 314 to provide power for these circuits during operation of the transponder 300.

The microprocessor 316 is programmed to perform either the function of transponder P or transponder S, described above in connection with FIG. 1. The receive circuit 314 of the onboard circuit 501 also communicates with the processor 316 over a communication bus 518 to facilitate the processing of received signals from the external operator station having the CPU 112. The input of the receive circuit 314 connects to the three receive coils $L_7$, $L_8$, and $L_9$, which are electrically connected in parallel at nodes 520 and 522 as a receiving antenna, the nodes 520 and 522 being the inputs of the receive circuit 314, to improve the potential for coupling a signal transmitted from the operator station according to any orientation of the transponder 300 during operation. The transmit circuit 320 also communicates with the processor 316 over a communication bus 524 to facilitate the transmission of data and signals to the operator station via transmit coils $L_4$, $L_5$, and $L_6$, which are electrically connected in parallel across node 526 and 528 as a radiating antenna, the output nodes of the transmit circuit 320. In the case of transponder P, the transmitter circuit 320 is tuned to transmit the range signal at frequency $f_2$. The receive circuit 314 can be tuned to receive the data signal at frequency $f_3$, or can be tuned to another frequency for communicating with the processor 316. In the case of transponder S, the circuitry 501 is modified so that transmit circuit 320 is tuned to transmit signals at the frequency $f_3$ and the receive circuit 314 is tuned to receive signals at the frequence $f_2$. The processor 316 of transponders P and S are uniquely programmed to perform the functions described hereinabove, or are operable to process received commands from the CPU 112 to provide such functions.

It will be appreciated that the disclosed architecture permits a relatively precise measurement of the distance D between transponders P and S using the attenuation of the received signal as the basis for the measurement. Similarly, the distance from the CPU 112 to a transponder, such as transponder P, can be determined using such signal attenuation technique. It should be noted that there may be some variations in the attenuation aspect and the measurement thereof due to the fact that the medium can change the attenuation. As such, it may be necessary to utilize a calibration procedure. In this procedure, a finite distance is noted between the two transponders S and P, and then an "offset" is determined. Therefore, the attenuation level is first measured from the transponder P, and this attenuation level can be correlated to a known distance and the relative difference therebetween determined.

Referring now to FIG. 6, there are illustrated additional details of the semiconductor structure of the transponder 300. The transponder 300 is hermetically protected by a thin exterior glass passivation layer 602, which may be PSG. The interior of the transponder 300 comprises the semiconductor substrate 303, which may be doped P-type or N-type in accordance with the particular requirements of the fabrication process. Optionally, the substrate 303 may be connected to the medical apparatus or other metallic intraluminal device to serve as a ground potential for the transponder 300. A large number of transistors T make up the circuitry of the power regulator 310, processor 316, and RF transmitter/receiver circuits 320 and 314, respectively, described above in connection with FIG. 5. Although these transistors T are schematically depicted as MOS transistors, the integrated circuitry of the transponder 300 could also use bipolar transistors. The individual transistors T are shown separated by portions of a field oxide layer 608. Transistor gates G and circuit interconnections (not shown) are embedded in an inter-level dielectric layer 600, and are made using conventional semiconductor fabrication techniques adapted to the spherical surface of the transponder 300.

One of the coils 603 (similar to coils $L_1$–$L_9$ described in connection with FIG. 5), is shown as having a plurality of separate windings 603a, 603b, 603c, and 603d which may be fabricated from a deposited layer of aluminum (or copper) that is patterned and etched using conventional semiconductor fabrication techniques adapted to the spherical shape of the transponder 300. The windings are insulated from each other by portions of the inter-level dielectric layer 600. The actual number of individual windings of the coil may be far greater than the four specific windings shown. The ends of the coil 603 are connected by additional conductors (not shown) to other circuit elements of the transponder 300.

Lineal Measurements

Referring now to FIG. 7, there is illustrated an alternative embodiment where transponders are used in the fingertips of surgical gloves. In this particular embodiment, a sterile examining glove 706 worn on the hand of a medical practitioner comprises a conventional plastic material. However, the tips of the index and middle fingers are modified to include respective transponders P and S, similar to those described hereinabove. The transponders P and S are operable to communicate with each other and with the CPU 112, preferably using circuitry generally described in connection with FIG. 5, and implemented on a transponder 300, as described above in connection with the FIG. 3.

The glove 706 can be useful in various procedures. For example, during childbirth it is important to know the size of the pelvic opening (or birth canal) to determine whether it is adequate for passage of the fetus during delivery. It is conventional practice for the attending physician, wearing a sterile glove, to estimate the size of the pelvic opening by extending the index and middle fingers into the birth canal to palpate the woman's ischial bone. This procedure is inherently inaccurate since the physician has to estimate the measurement by palpation. Since the decision whether or not to undergo a caesarean section is based in part on the estimated size of the birth canal, greater accuracy would improve the decision-making process.

Using the glove 706, the physician follows essentially the same procedure as with a conventional glove. However, by activating the positioning system disclosed herein, the distance between the transponders P and S at the respective tips of the index and middle fingers can be determined. When the physician touches the opposite points of the ischial bone in the birth canal, an accurate measurement of the distance D between transponders P and S can be read on the display 116.

Another application related to childbirth can take advantage of the disclosed position sensing system. The physician can implant transponders directly into the tissue of the cervix at an early stage of delivery. The transponder P can be implanted on one side of the cervix and the transponder S can be implanted on the opposite side of the cervix. Thus, the dilation of the cervical opening can be measured directly, and periodically observed on the display 116 as labor during childbirth progresses.

Position Of Vital Structures To A Cutting Instrument

Referring now to FIG. 8, there is illustrated an alternative embodiment where a transponder is used as a proximity warning device during surgery. During an abdominal surgical procedure, a scalpel or other cutting instrument 800 can be modified to include a primary transponder P installed within the instrument 800 adjacent to its cutting tip 802. Certain vulnerable vessels 804 such as a ureter, a blood vessel, or even a duct within the abdominal cavity can be protected from inadvertent damage by the cutting instrument 800 by installing a catheter 806 within such a vessel 804. The catheter 806 may be employed with multiple secondary transponders $S_1$, $S_2$, $S_3$ and $S_4$ attached thereto, and placed into the ureter through the urethra and bladder in a retrograde fashion. This allows position determination of the ureter during the surgery. The secondary transponders $S_1$, $S_2$, $S_3$ and $S_4$ may be spaced at desired intervals in the wall of the catheter 806 to provide an array of proximity sensors along the contours of the vessel 804 or duct.

A safe distance proximity value L may be set in memory in the CPU 112 using the operator control panel 114. For example, a proximity value of two centimeters (L=2.0) may be selected such that during surgery, if the tip 802 of the cutting instrument 800 comes within two centimeters of any of the secondary transponders $S_1$, $S_2$, $S_3$ or $S_4$, the alarm 120 is sounded to alert the surgeon to exercise caution in cutting tissue in that vicinity, and to be alert to the presence of the vessel 804 while the alarm 120 is sounding. An example of a suitable alarm 120 could be a beeper that ordinarily beeps at one second intervals, but when the primary transponder P in the tip 802 of the surgical cutting instrument 800 comes within the preset safe distance proximity value L of one of the secondary transponders $S_1$, $S_2$, $S_3$ or $S_4$, the alarm 120 will beep more rapidly, and perhaps more loudly, either as a step or in increasing rapidity and loudness as the distance L decreases to forewarn the surgeon of the proximity of the cutting instrument tip 802 to the vessel 804.

An external proximity unit (EPU) operable to communicate with the transponders P and S, and in conjunction with the display unit 116, can provide the surgeon this distance L. The EPU may also provide the audible alarm and messaging such that the surgeon need not glance away to display 116 to ascertain the current position of the tip 802 of the cutting instrument 800 to the vital structure. Thus, the surgeon can avoid injury to the vital structures.

Figure 9:
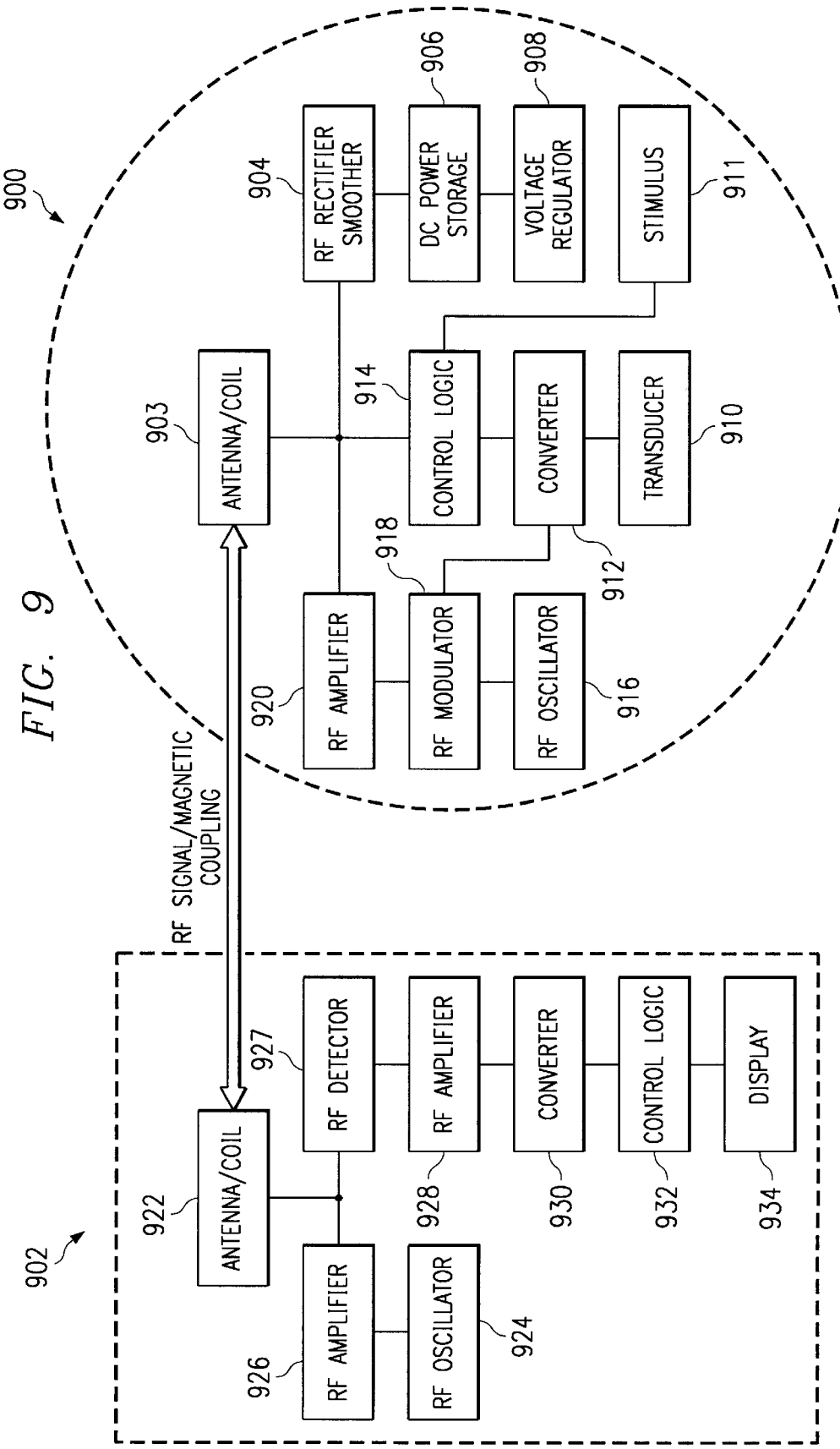
FIG. 9 illustrates a more detailed block diagram of an alternative embodiment of a control system and transponder.

Referring now to FIG. 9, there is illustrated a more detailed block diagram of an alternative embodiment of a control system and transponder having more complex integrated circuitry. The transponder 900 (similar to transponders P and S, and transponder 300) includes circuitry for receiving power by magnetic coupling and transmitting data by RF transmission to a remote receiver in an external monitoring station 902 (similar to the external system of system 100 which comprises the CPU 112, alarm 120, display 116, and operator panel 114). The basic circuit functions performed by the semiconductor transponder ball 900 are illustrated, and designated generally by reference numeral 900, which communicates with the monitoring station 902.

The transponder 900 includes an antenna/coil 903, which serves the dual purpose of receiving power from the station 902 and transmitting data on an RF carrier signal to the station 902. The power may be received by the antenna/coil 903 by direct magnetic coupling, if the station 902 is sufficiently close to the transponder 900. Alternatively, an electromagnetic wave can be used to transmit power from the station 902 to the transponder 900, whereby the magnetic field component of the electromagnetic wave induces a current in the coil 903, in accordance with known techniques. The power signal received by the antenna/coil 903 is rectified and smoothed by an RF rectifier smoother circuit 904. The output of the rectifier circuit 904 is connected to a DC power storage device 906, such as a capacitor. Such capacitor might also be of assistance in performing the waveform smoothing function. A voltage regulator 908 is used to make the DC voltage stable regardless of the distance between the station 902 and the transponder 900. For example, a Zener diode or other suitable clamping circuit can perform this function. The resulting DC voltage is supplied to all circuits of the transponder 900.

In this particular embodiment, the transponder 900 may also include at least one transducer 910, which may be a sensor or an actuator. It will be appreciated that more than one sensor or actuator can be constructed on the transponder 900. In the case of a sensor, a condition or parameter of the environment in which the transponder 900 is located is sensed. For example, pressure can be sensed through a change in capacitance or resistance. Such semiconductor pressure transducers are known in the art and can be adapted to fabrication on the spherical semiconductor substrate 303. A variable-resistance strain gauge is disclosed in commonly-assigned U.S. patent application Ser. No. 09/448,641, entitled "Intraluminal Monitoring System," and filed on Nov. 24, 1999, which is hereby incorporated by reference. In the case of multiple sensors on a single transponder 900, more than one condition or parameter of the environment of the transponder 900 is sensed. For example, temperature, as well as pressure sensing, and electrical stimulation can be provided by suitable means on a single transponder 900. In the case of an actuator, a stimulus circuit 911 applies an electrical stimulus under control of the control logic 914 to the tissue or medium in which it comes in contact, during the position sensing function, and while the temperature of the surrounding tissues is being measured. For example, a certain medical procedure may require that stimulus be provided to an anatomical structure to increase or decrease separation from another structure. Using the disclosed position sensing system in cooperation with an onboard stimulus generator can facilitate this type of medical procedure. A separate actuator signal may need to be transmitted to the transponder 900, in addition to the power signal for powering the transponder 900. The transmitted actuator signal is then processed by an onboard control logic circuit 914 to control the stimulus circuit 911 to perform the desired function.

A converter 912, which may be an A/D converter, is used to convert the condition sensed by the transducer 910 to a signal that can be transmitted out to the station 902. The converter 912 can be part of the transducer 910 (e.g., a pressure transducer such as a variable capacitor for generating a signal depending upon the variations in capacitance). The control logic 914, which can be part of an onboard processor that controls not only the converter 912, but also other circuitry on the transponder 900, is provided in accordance with known techniques. An RF oscillator 916 generates a radio-frequency carrier signal at a predetermined frequency in the RF band. An RF modulator 918 modulates the output of the converter 912 onto the carrier frequency signal. The resulting modulated signal is amplified by RF amplifier 920, and then transmitted external to the body through the antenna/coil 903. The illustrated antenna/coil block 903 represents one or more of the coil sets 302, 304, and 306, the power, transmit and receive coils $L_1$–$L_9$.

The monitoring station 902 includes an antenna/coil 922 that serves the dual purpose of generating the electromagnetic wave for transmitting power to the transponder 900, and receiving the RF data signal transmitted by the transponder 900. It is preferred that the frequency of the electromagnetic wave that is output by the antenna/coil 922 is different from the carrier frequency generated by an RF oscillator 924. An RF amplifier 926 is used to couple the electromagnetic wave for power transmission to the antenna/coil 922. The frequency of the electromagnetic wave that is output by the station 902 is determined by the RF oscillator 924. The data signal received by the antenna/coil 922 is detected by an RF detector 927 and then amplified by an RF amplifier 928. Preferably, the signal from the RF amplifier 928 is converted by a converter 930 to a digital signal, which in turn is input to control logic 932. The control logic 932 may be a special-purpose CPU, or an interface to a general-purpose CPU or computer. The control logic 932 extracts the data from the signal received by the station 902 from the transponder 900, and displays that information on a suitable display 934, such as a CRT screen. The technique for transmitting data from the transponder 900 to the station 902 using the carrier frequency generated by the RF oscillator 916, can be in any form, using any suitable protocol. The modulation can be, for example, AM, FM, PM or any other suitable modulation technique.

Although a single transponder 300 can include the foregoing functions, more complex monitoring functions with multiple transducers can be implemented using multiple ball systems attached to catheters, needles and other insertable devices. These systems can be affixed to body surfaces, or can be attached to catheters, needles, and other insertable devices. In the case of insertable devices, these systems can be arranged so as to remain fixed at a specified site, or can be permitted to be transported through body conduits by various means, including convection, peristalsis, diffusion, etc.

Figure 10:
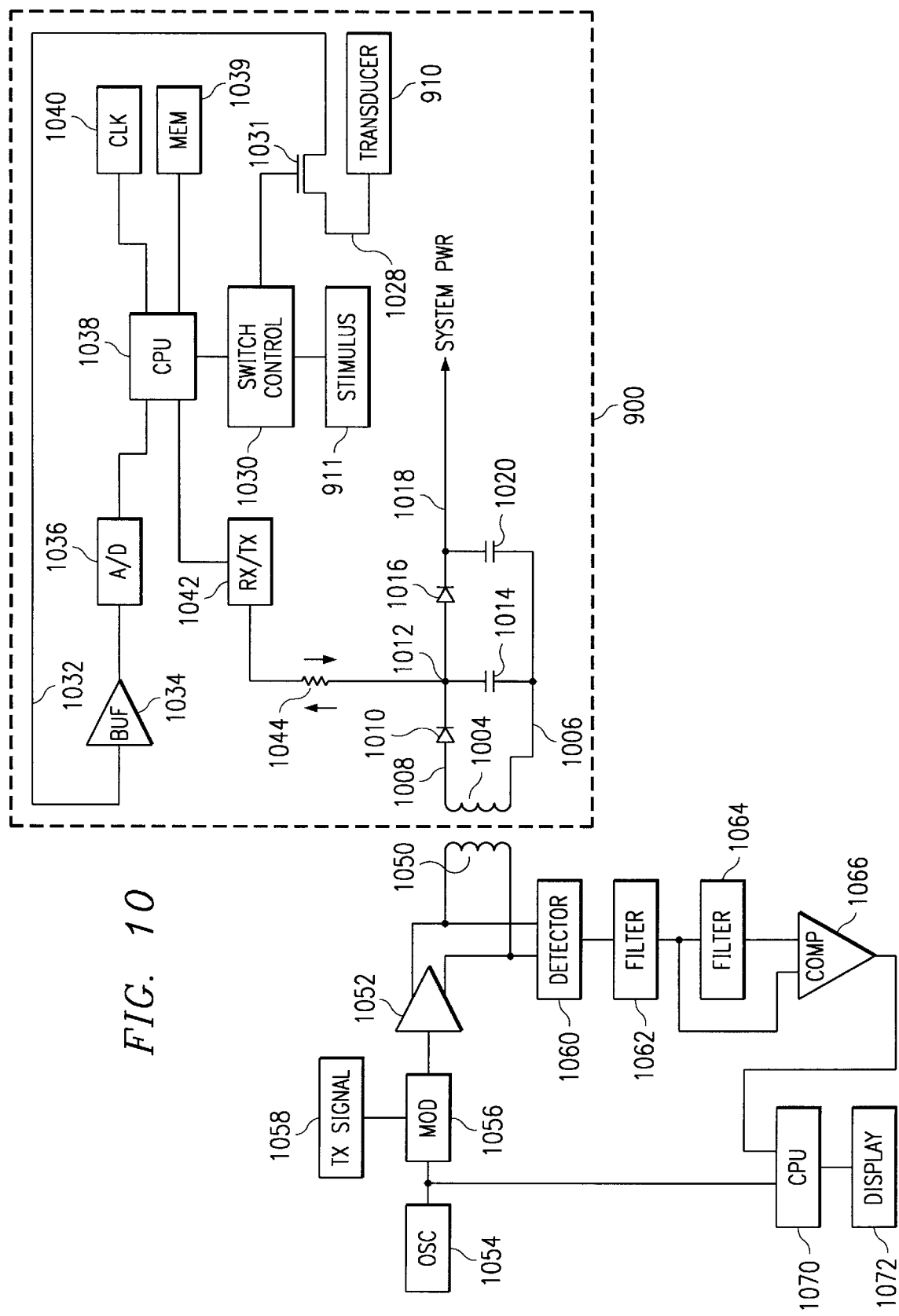
FIG. 10 illustrates a schematic block diagram of the transponder and the control system of FIG. 9.

Referring now to FIG. 10, there is illustrated a schematic block diagram of the transponder 900 and the control system 902 of FIG. 9. The ball transponder 900 (similar to ball transponders P and S, and transponder 300 described hereinabove), is operable to provide the transmit/receive functions associated with a disclosed transponder embodiment, the transducer 910 for interfacing with the desired quantitative condition, and the stimulus circuit 911 for stimulating the desired body tissues. The illustrated embodiment of FIG. 10 is that associated with a "passive" system, which term refers to a system having no battery associated therewith. In order to operate the system, there is provided an inductive coupling element 1004 in the form of an inductor, which is operable to pick up an alternating wave or impulse via inductive coupling, and extract the energy therein for storage in the inductive element 1004. This will create a voltage across the inductive element 1004 between a node 1006 and a node 1008. A diode 1010 is connected between the node 1008 and the node 1012, with the anode of diode 1010 connected to node 1008 and the cathode of diode 1010 connected to a node 1012. Typically, the diode 1010 will be fabricated as a Schottky diode, but can be a simple PN semiconductor diode. For the purposes of this embodiment, the PN diode will be described, although it should be understood that a Schottky diode could easily be fabricated to replace this diode. The reason for utilizing a Schottky diode is that the Schottky diode has a lower voltage drop in the forward conducting direction.

The diode 1010 is operable to rectify the voltage across the inductive element 1004 onto the node 1012, which has a capacitor 1014 disposed between node 1012 and node 1006. Node 1012 is also connected through a diode 1016 having the anode thereof connected to node 1012 and the cathode thereof connected to a node 1018 to charge up a capacitor 1020 disposed between node 1018 and 1006. The capacitor 1020 is the power supply capacitor for providing power to the transponder 900. The capacitor 1014, as will be described hereinbelow, is operable to be discharged during operation of the system and, therefore, a separate capacitor, the capacitor 1020, is required for storing power to power the system of the transponder 900.

There is also provided a switching transistor 1031 which has one side of the gate/source path thereof connected to a node 1028, which is the output of the transducer 1015 and the other side thereof connected to a node 1032. The gate of transistor 1031 is connected to the output of a switch control 1030. Node 1032 is connected to the input of a buffer 1034 to generate an analog signal output thereof which is then converted with an analog-to-digital converter 1036 to a digital value for input to a CPU 1038 (comprised in control logic 914, and similar to processor 316). The CPU 1038 is operable to receive and process this digital input voltage. A clock circuit 1040 provides timing to the system. A memory 1039 is provided in communication with the CPU 1038 to allow the CPU 1038 to store data therein for later transmittal back to the control system 902 or for even storing received instructions. This memory 1039 can be volatile or it can be non-volatile, such as a ROM. For the volatile configuration, of course, this will lose all information when the power is removed. The memory 1039 is also operable to store pre-programmed information such as a unique ID, patient information, physician information, or any information desired according to the particular procedure and function of the transponder 900. The CPU 1038 is operable to provide control signals to the switch control 1030 for turning on the transistor 1031 at the appropriate time. In addition to the transistor 1031 being toggled to read the transducer 910, transistor 1031 could be a pass-through circuit such that the CPU 1038 can continually monitor the voltage at the output of the transducer 910. The control switch 1030 can also switch current to the stimulus circuit 911 to stimulate the desired contacted tissue. System power to all power-consuming elements of the ball transponder 900 is provided at the SYSTEM PWR output node.

In order to communicate with the CPU 1038 for transferring data thereto and for allowing the CPU 1038 to transfer data therefrom, a receive/transmit circuit 1042 (similar to the receive and transmits circuit 314 and 320, respectively) is provided for interfacing to node 1012 through a resistive element 1044. This allows RF energy to be transmitted to node 1012. It is important to note that the semiconductor junction across diode 1010 is a capacitive junction. Therefore, this will allow coupling from node 1012 to node 1008. Although not illustrated, this could actually be a tuned circuit, by selecting the value of the capacitance inherent in the design of the diode 1010. In any event, this allows an RF connection to be provided across diode 1010 while allowing sufficient energy to be input across conductive element 1004 to provide a voltage thereacross for rectification by the diode 1010 and capacitor 1014. Typically, the frequency of this connection will be in the MHz range, depending upon the design. However, many designs could be utilized. Some of these are illustrated in Beigel, U.S. Pat. No. 4,333,072, entitled "Identification Device," issued Jun. 1, 1982, and Mogi et al., U.S. Pat. No. 3,944,982, entitled "Remote Control System For Electric Apparatus," issued Mar. 16, 1976, which are incorporated herein by reference. With these types of systems, power can continually be provided to the node 1012 and subsequently to capacitor 1020 to allow power to be constantly applied to the ball transponder 900.

The external control system 902, which is disposed outside of the body and proximate to the ball transponder 900, includes an inductive element 1050 which is operable to be disposed in an area proximate to the skin, yet exterior to the body, in the proximity of the transponder 900. The inductive element 1050 is driven by a driving circuit 1052 which provides a differential output that is driven by an oscillator 1054. This will be at a predetermined frequency and power level necessary to couple energy from inductive element 1050 to inductive element 1004. Since this is an external system, the power of the oscillator can be set to a level to account for any losses through the body tissues. To allow information to be transmitted, a modulation circuit 1056 is provided which is modulated by a transmitter signal in a block 1058 that allows information to be modulated onto the oscillator signal of the oscillator 1054, which oscillator signal is essentially a "carrier" signal. However, it should be understood that the information that is transmitted to the transponder 900 could merely be date information, whereas the CPU 1038 could operate independent of any transmitted information to provide the correct timing for the output pulses and the correct waveshape therefor.

Alternatively, entire control of the system could be provided by the transmit signal 1058 and the information carried thereon, since power must be delivered to the illustrated embodiment due to the lack of any independent power in the transponder 900. Note also that the distance of the remote system 902 to the transponder 900 may need to be varied such that the power signal coupled to the transponder 900 is of sufficient energy to receive an RF signal back from the transponder 900. The strength of the signals exchanged between the transponder 900 and the control system 902 varies according to the number of tissues and body parts between the transponder 900 and the control system 902. For example, where a transponder 900 is introduced in a vein close to the surface of the skin, the signal strength is less likely to be affected since the control system 902 can be placed very closely to the transponder 900. On the other hand, where the transponder 900 is introduced into an artery near the heart, the signal strength of the control system 902 may need to be increased to power the transponder 900. Alternatively, where the power output of the control system 902 is limited, the antenna mechanism 118 may need be inserted into the body to come into closer proximity of the transponder 900.

When the information is to be transmitted from the transponder 900, it is superimposed upon the oscillator signal driving the inductive element 1004 and coupled across to the control system antenna inductor element 1050. This is extracted therefrom via a detector 1060 which has the output thereof input to a first low pass filter 1062, and then to a second low pass filter 1064. The output of low pass filters 1062 and 1064 are compared using a comparator 1066 to provide the data. The filter 1062 provides an average voltage output, whereas the filter 1064 provides the actual digital voltage output. The output of the comparator 1066 is then input to a CPU 1070 which also is powered by the oscillator 1054 to process the data received therefrom. This can then be input to a display 1072.

Figure 11A:
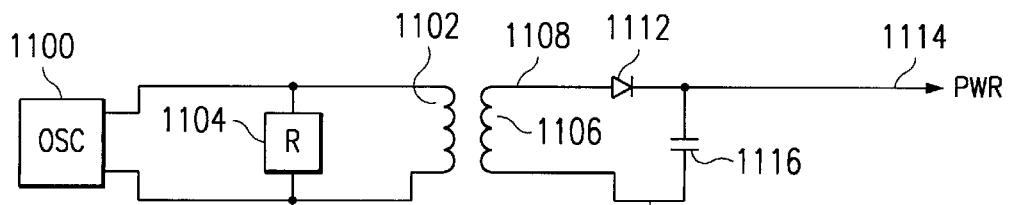
FIGS. 11A–11C illustrate alternate embodiments for the transmit/receive operation.
Figure 11B:
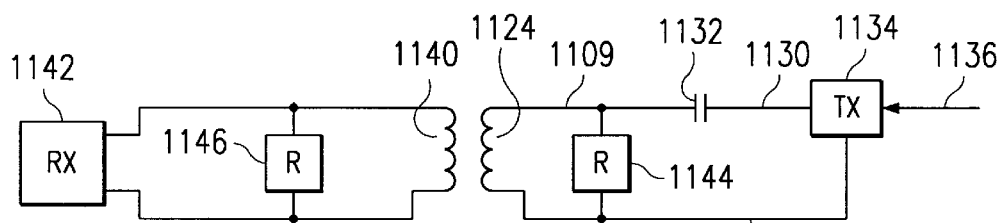
Figure 11C:
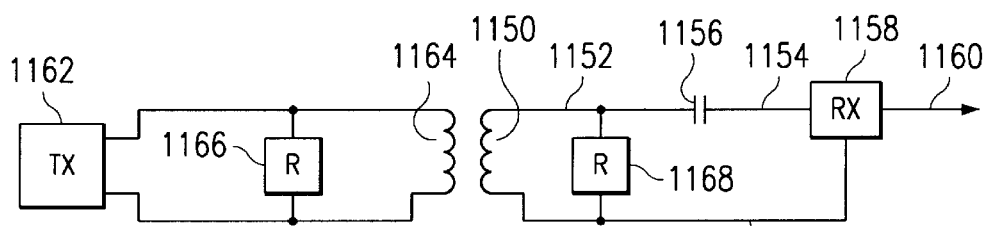

Referring now to FIGS. 11A–11C, there are illustrated alternate embodiments for the transmit/receive operation. In FIG. 11A, there is provided an oscillator 1100 which drives an external inductive element 1102. Typically, there is some type of load 1104 disposed across the inductive element 1102. This is the primary power that is provided to the system. A separate inductive element 1106 is provided on the transponder 900, for being inductively coupled to the inductive element 1102. Thereafter, a voltage is generated across the inductive element 1106, the inductive element 1106 being connected between nodes 1108 and 1110. A diode 1112 is connected between node 1108 and a power node 1114, and a power supply capacitor 1116 is disposed across node 1114 and a node 1110. This allows the voltage on node 1108 to be rectified with diode 1112.

In the alternative embodiment of FIG. 11B, the receive operation utilizes a separate inductive element or antenna 1124 in the transponder 900, which is operable to be connected between nodes 1109 and 1111. Node 1109 is capacitively coupled to a transmit node 1130 with a capacitor 1132, the capacitor 1132 being a coupling capacitor. A transmitter 1134 is provided for transmitting received data from a line 1136 to the node 1130, which is then coupled to the node 1109 to impress the RF signal across the inductive element 1124.

A corresponding inductive element 1140 is disposed on the external control system 902, which inductive element 1140 is operable to be disposed proximate to the inductive element 1124, but external to the human body. The inductive element 1140 is basically a "pick-up" element which is operable to receive information and function as an antenna, and provide the received signal to a receiver 1142. The structure of FIG. 11B is a separate structure, such that node 1109 is isolated from node 1108, the power receiving node. However, it should be under stood that any harmonics of the oscillator 1110 would, of course leak over into the inductive element 1124. This can be tuned out with the use of some type of tuning element 1144 on the transponder 900 disposed across inductive element 1124, and also a tuning element 1146 disposed across the inductive element 1140, i.e., the antenna.

Referring now to FIG. 11C, there is illustrated a simplified schematic diagram of the receive portion. The transponder 900 has associated therewith a separate receive antenna or inductive element 1150 disposed between node 1113 and a node 1152. Node 1152 is capacitively coupled to a receive node 1154 with a coupling capacitor 1156. A receiver 1158 is provided for receiving the information transmitted thereto and providing on the output thereof data on a data line 1160. The receiver 1158 is operable to receive the RF signal, demodulate the data therefrom, and provide digital data on the output 1160. External to the human body and the transponder 900 is a transmitter 1162 which is operable to impress a signal across an external inductive element 1164. The inductive element 1164 basically provides the RF energy and is essentially tuned with a tuning element 1166. A corresponding tuning element 1168 is provided on the transponder 900 and disposed across inductive element 1150, the inductive element 1150 acting as an antenna, as well as the inductive element 1164.

Note that in circumstances where the signals of the transponder 900 cannot be adequately received therefrom and/or power coupled thereto, selected portions of all of the external location circuitry 902 may need to be inserted into the body proximate to the transponder 900 in order to couple the transmit/receive signals and power. Furthermore, where more than transponder 900 is used, communication of power and data signals between the various transponders 900 may need to employ distinct time periods (i.e., time multiplexing) when communication occurs using a single common frequency, or discrimination circuits may need to be used where communication occurs simultaneously with the plurality of implanted transponders 900 having different oscillator frequencies.

Figure 12:
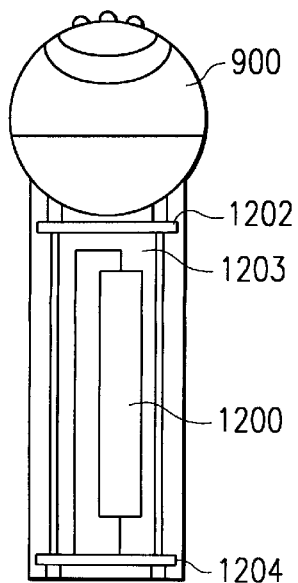
FIG. 12 illustrates a physical side view of an alternative embodiment utilizing additional circuitry or structure attached to the transponder for providing a local power source.

Referring now to FIG. 12, there is illustrated a side view of an alternative embodiment utilizing additional circuitry or structure attached to the transponder 900 for providing a local power source. As described hereinabove, the transponder 900 requires a power-generating structure for storing a power supply voltage such that diodes must be provided for receiving and rectifying a large amount of power and charging up a power supply capacitor. Alternatively, the transponder 900 could be configured to interface to an attached power supply system 1200 comprising either a battery or a capacitor. The local power supply system 1200 is illustrated as disposed on a circuit board 1203 defined by supporting structures 1202 and 1204. The circuit board 1203 contains electronics for interfacing the local power supply system 1200 to the transponder 900. Furthermore, the small battery 1200 can be installed with the transponder P in place of a power receiving coil.

Figure 13:
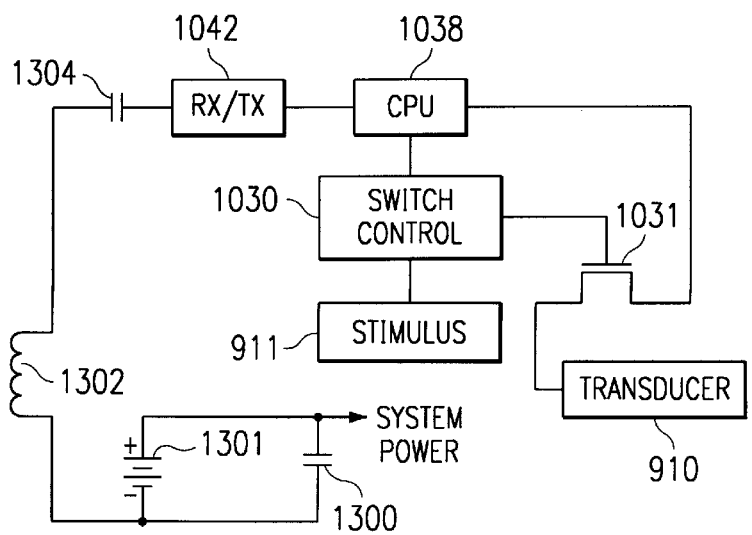
FIG. 13 illustrates a schematic block diagram of the transponder using a battery as the local power supply system.

Referring now to FIG. 13, there is illustrated a schematic block diagram of the transponder 900 using a battery as the local power supply system 1200. A battery 1301 is provided as a source of self-contained power and is connected across a capacitor 1300 to providing smoothing of any power output to the system power-consuming elements of the transponder 900. Power for all onboard components is obtained from the SYSTEM POWER output by providing sufficient charge to the capacitor 1300. The capacitor 1300 could be formed on the surface of the transponder 900 or it could actually be part of the battery structure 1301. Additionally, the capacitance 1300 could actually be the capacitance of the battery 1301. Additional structure could be provided for powering the CPU 1038 and the other circuitry on the transponder 900 from the battery 1301. As such, there would only be required a smaller inductive element 1302 and a capacitor 1304 to allow the receive/transmit block 1042 to receive/transmit information from and to the external control system 902. The switch control 1030 controls the gate of the switching transistor 1031 to switch output of the transducer 910 through the switching transistor 1031 source/drain path to the CPU 1038. The switch control 1030 also switches output power to the stimulus circuit 911 for stimulating tissues or medium.

Figure 14:
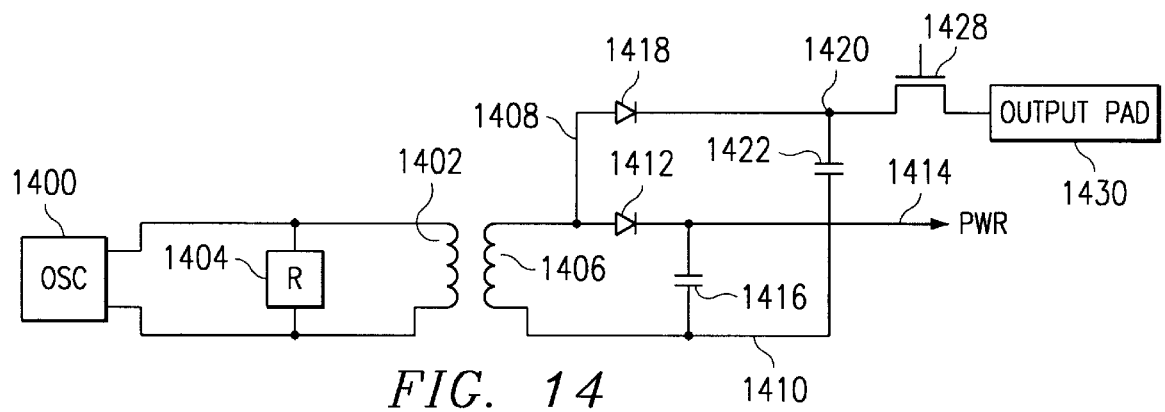
FIG. 14 illustrates alternate embodiments for the transmit/receive operation of a stimulus circuit.

Referring now to FIG. 14, there are illustrated alternate embodiments for the transmit/receive operation of a stimulus circuit. There is provided an oscillator 1400 which drives an external inductive element 1402 which may be utilized to couple both electrical power and information or data. Typically, there is some type of load 1404 disposed across the inductive element 1402. A separate inductive element 1406, inductively coupled to inductive element 1402, is provided on the transponder 900. Voltage generated across the inductive element 1406, connected between a node 1408 and a node 1410, is applied across rectifier 1412 connected between node 1408 and a power node 1414. A power supply capacitor 1416 disposed across node 1414 and node 1410 stores the rectified voltage for use by the circuit. Similarly, a rectifier 1418 is connected between the node 1408 and a node 1420 which is connected to one side of a main "surge" capacitor 1422. The other side of capacitor 1422 is connected to node 1410. The switching transistor 1428 is provided for connecting the node 1420 to an output stimulus pad 1430. The receive/transmit circuits (not shown) are identical in structure to that illustrated in FIGS. 11B and 11C.

Referring now to FIG. 15, there is illustrated a side view of an alternative embodiment of a transponder utilized in conjunction with a stimulus function. In one application, the transponder 1500 requires two primary structures 1502 and 1504 to operate as the anode and cathode stimulus leads. The transponder 1500 comprises an interstitial structure 1506 for storing a power supply voltage. Therefore diodes must be provided for receiving and rectifying a large amount of power and charging up a power supply capacitor, in addition to a main "surge" capacitor for providing a relatively large amount of pulsed energy to desired tissues. The interstitial structure 1506 may contain either a battery or a capacitor to provide this stimulus power, as represented by a structure 1508, and which is supported between supporting structures 1510 and 1512.

Figure 16:
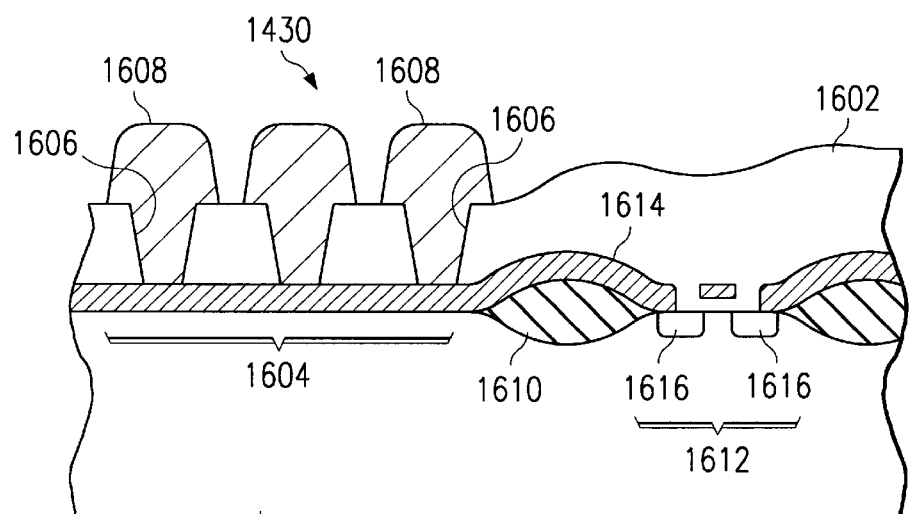
FIG. 16 illustrates a cross-sectional view of an output pad, in an alternative embodiment where a stimulus is employed.

Referring now to FIG. 16, there is illustrated a cross-sectional view of an output pad 1430, in an alternative embodiment where a stimulus is employed. In general, an output pad 1430 (similar to stimulus leads 1502 and 1504) is required to provide a conductive interface between the transistor 1428 and, for example, the desired tissue. This therefore requires some type of metallic interface that is non-reactive. Such an interface would require a metal such as gold, platinum and the like. In the disclosed embodiment, gold would be provided. After the formation of the upper metal layer via a deposition technique with metal such as aluminum or copper, a passivation layer of oxide 1602 is disposed over the substrate to basically prevent oxidation of the metal layers and protect the semiconductor circuits in general. The contact layer 1614 extends beyond the active region 1612 to an output pad region 1604 and is separated from the active region 1612 by a layer of field oxide 1610 or some type of isolation oxide formed on a substrate 1601. There may be some type of channel stop implant disposed below the field oxide layer 1610. The contact 1614 extends from the source/drain implant 1616 to the region 1604. This contact 1614 is required to be fairly conductive. Typically, polycrystalline silicon is not of sufficient conductivity to meet this requirement. Therefore, some type of polysilicide process will be required, wherein the upper surface is converted to some type of silicide such as titanium disilicide to lower the surface resistivity thereof. Alternatively, a metal layer could be provided which is connected to the contact region 1614.

Once the contact 1614 is formed and the passivation layer 1602 is disposed over the entire structure, vias 1606 are formed therein. These vias are then filled with metallic plugs 1608 by forming a layer of metal over the oxide layer 1602 and then etching the oxide layer 1602 to remove the undesired portions. The metal plugs 1608 may be formed of metal such as aluminum or gold. If they were formed of gold, this would allow for soldering if they were to be used as contacts. However, in this context, these plugs 1608 are utilized for conductivity purposes. Therefore, an aluminum plug would be sufficient if it were covered with a thin layer of gold to render the aluminum non-reactive and prevent oxidation thereof. Alternatively, in the disclosed embodiment, the plug 1608 may, of course, be gold. However, it should be understood that any type of non-reactive metal could be utilized as long as the surface thereof is sufficiently non-reactive, and the conductance of the plug 1608 is sufficiently high to result in a low resistance path between the exterior of the transponder 900 and a capacitive plate (not shown). The reason for this is that the stored charge must be discharged into a resistance as low as 500 ohms and any significant resistance disposed between the upper plate of the capacitor and the exterior must be minimized.

Figure 17:
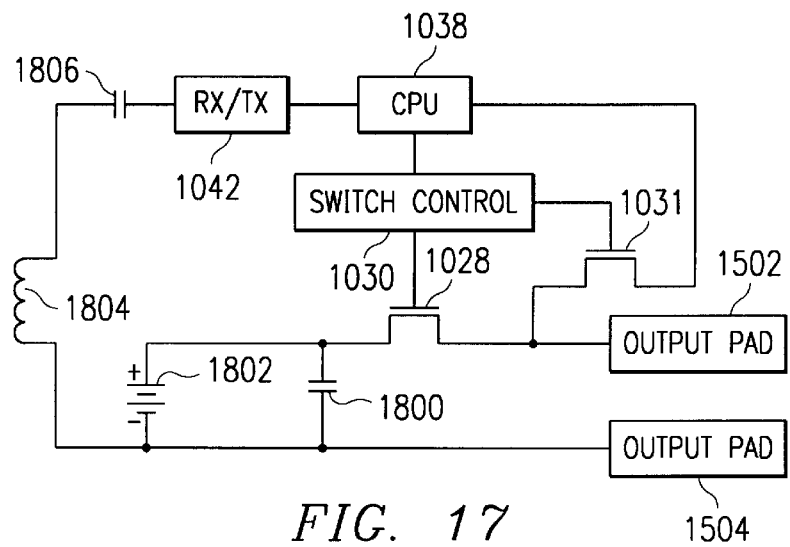
FIG. 17 illustrates a schematic block diagram of the stimulus circuit 911 of FIG. 9 with the use of a battery.

Referring now to FIG. 17, there is illustrated a schematic block diagram of the stimulus circuit 911 with the use of a battery. A battery 1802 is provided which is connected to a capacitor 1800. The capacitor 1800 could be formed on the surface of the transponder 900, or it could actually be part of the structure 1508 shown in FIG. 15. The battery 1802 is connected across the capacitor 1800 to provide sufficient charge therefor. Additionally, the capacitance 1800 could actually be the capacitance of the battery 1802. Additional structure could be provided for powering the CPU 1038 and the other circuitry on the chip from the battery 1802. As such, there would only be required a smaller inductive element 1804 and a capacitor 1806 to allow the receive/transmit block 1042 to receive/transmit information from and to the exterior control station 902. The switch control 1030 controls the switching transistors 1028 and 1031 which provide a current path to the stimulus leads 1502 and 1504 (similar to output pad 1430), which contact the desired tissue.

Stereotactic Surgical Navigational Guidance System

Frequently, precise location of microscopic or gross surgical instruments is required in order to prevent damage to vital structures. For example, in neurosurgical procedures where malignancies may be located adjacent to vital structures precise instrument navigation is critical.

Figure 18:
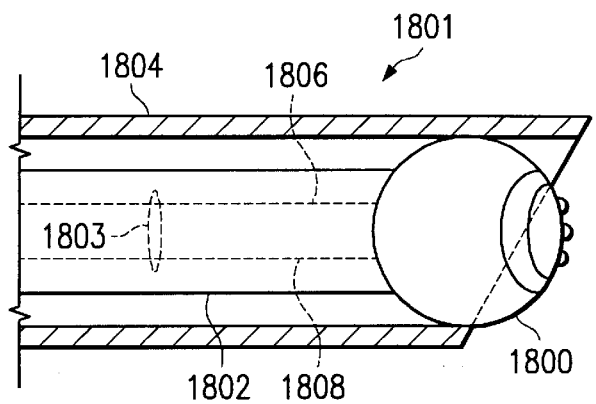
FIG. 18 illustrates a surgical needle assembly having a transponder positioned on the end of a guidewire which is inserted through down a hollow bore surgical needle shaft.

Referring now to FIG. 18, there is illustrated a surgical needle assembly 1801 having a transponder 1800 positioned on the end of a guidewire 1802 which is inserted through and down a hollow bore surgical needle shaft 1804. The guidewire 1802 with transponder 1800 can be removed, and surgical instruments inserted down the shaft 1804. In this embodiment, the transponder 1800 is a passive system whereby the transponder 1800 operates only in response to being powered and queried from the external control system 100. Optionally, the transponder 1800 may be constructed to have hardwire connections 1803 which extend back through the guidewire to external electronics by introducing a ground terminal connection 1806 and a data tenninal connection 1808. In this case, the ground terminal 1806 is electrically connected (not shown) to the metal annulus of the guidewire 1802 by a solder connection.

Figure 19A:
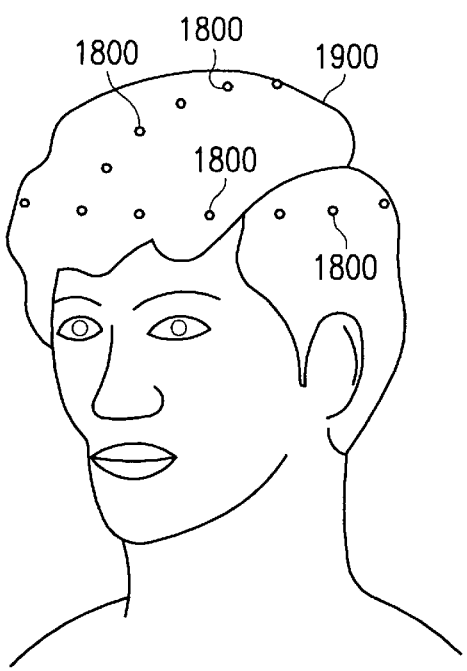
FIGS. 19A and 19B together illustrates a frontal view and a top cross-sectional view of a cranium having transponders located at multiple points on the outside of the cranium.
Figure 19B:
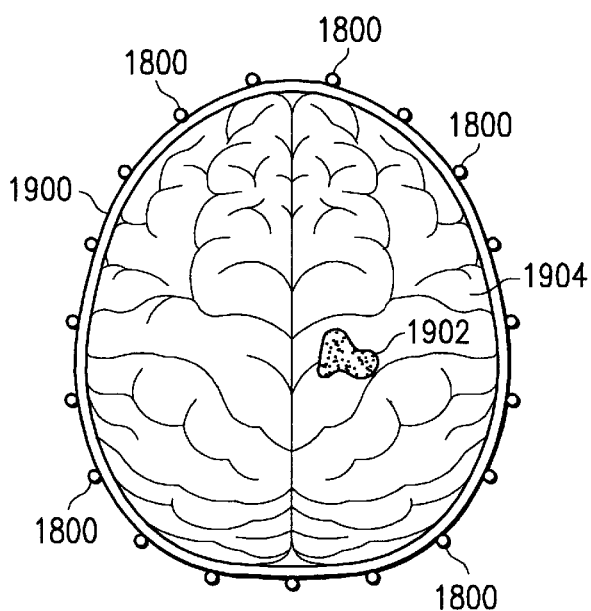

Referring now to FIGS. 19A and 19B, there are illustrated a frontal view and a top cross-sectional view of a cranium having transponders located at multiple points on the outside of the cranium. In this particular application, one or more transponders 1800 are positioned at multiple points on the external surface of a cranium 1900. The surgical needle assembly 1801 of FIG. 18 is inserted into malignant cerebral tissue 1902 under computerized axial tomography with robotic guidance under control of the CPU 112 based upon continuous readout of information received from each of the transponders 1800. The site of surgery is reached with minimal damage to surrounding cerebral tissue 1904. After the surgical needle assembly 1801 has been inserted into the malignant tissue 1902, the guidewire 1802 with attached transponder 1800 can be removed, and other surgical instruments inserted down the shaft 1804. At any point, the guidewire 1802 may be reinserted to determine the exact location of the end of the needle shaft 1804. Alternatively, another transponder 1800 may be attached to the surgical instrument being passed down the needle shaft 1804 to determine the real time location during the procedure performed with that particular surgical instrument. All transponders 1800 are in constant communication with a central processing unit 112. The central processing unit 112 guides the insertion of the surgical needle shaft 1804 into the cerebral tissue 1904 based on information received from all of the transponders 1800 implanted around the cranium 1900, the computerized axial tomography image, or any other type of imaging process. In further alternative embodiments, these transponders 1800 can be utilized for navigational guidance in any robotic surgical procedures.

When dealing with multiple transponders, it is necessary that each transponder have a unique ID and that the received signal therefrom be distinguishable. Therefore, the transponder that is associated with the surgical instrument moving through the tissue is required to transmit information therefrom in a relatively uniform pattern. Each of the transponders 1800 will then receive information in the form of the amplitude of the signal from the moving transponder. Each one of the transponders 1800 will then transmit this distance information, either in the form of an amplitude or in the form of a calculated distance, to the CPU 112. However, it is noted that "contention" can occur during this transmission. To facilitate this problem, each of the transponders 1800 can randomly transmit at a different time. It may be that the transmission is on a duty cycle of 1:10, i.e., for every one millisecond that the transmission is on, it is off for ten milliseconds. In this manner, the CPU 112 will "collect" information from transponders that happen to transmit by themselves with no interfering information from other transponders. Alternatively, there can be a plurality of receivers disposed about the cranium proximate to each of the transponders, wherein each of the transponders will transmit a very low level of power. Once all of this information is collected, and knowing the position of each of the sensors, then the position of the moving sensor can be "triangulated" upon.

Figure 20:
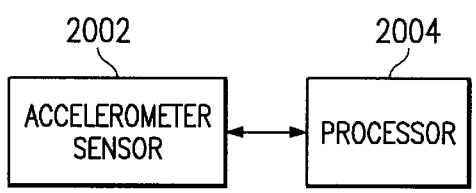
FIG. 20 illustrates a general block diagram of the accelerometer unit.

Referring now to FIG. 20, there is illustrated a simplified block diagram of an accelerometer sensor system of the present disclosure. There is basically provided an accelerometer sensor 2002 which is operable to sense both magnitude of acceleration and direction thereof. This accelerometer sensor 2002 is interfaced with a processor 2004, which processor 2004 is operable to interface with accelerometer sensor 2002 to perform the sensing operation and provide an output representing both magnitude and direction of the acceleration, as will be described hereinbelow.

Figure 21:
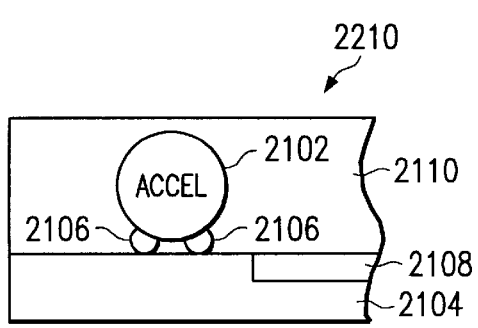
FIG. 21 illustrates a side view of the accelerometer unit of the present disclosure.

Referring now to FIG. 21, there is illustrated a side view of the physical embodiment of the accelerometer sensor 2002 and processor 2004. Accelerometer sensor 2002 is realized with a spherical semiconductor device and results in a spherical accelerometer sensor 2102, which is disposed on a processor substrate 2104 through the use of solder balls 2106. The processor 2104 has disposed thereon an integrated circuit section 2108, which integrated circuit section 2108 contains the circuitry associated with the processor 2004. The entire surface thereof can be encapsulated in an encapsulating layer 2110.

Figure 22:
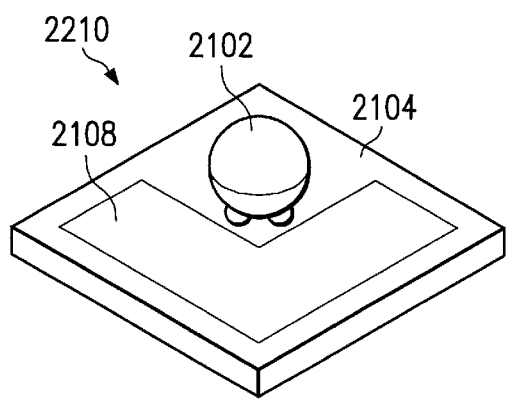
FIG. 22 illustrates a perspective view of the accelerometer sensor/processor combination.

Referring now to FIG. 22, there is illustrated a perspective view of the accelerometer sensor/processor combination of FIG. 21. It can be seen that the accelerometer sensor 2102 is disposed on a much larger substrate, the substrate 2104, which substrate is required for the purpose of containing sufficient processing circuitry in the circuitry section 2108 for interfacing with accelerometer sensor 2102. Depending upon the complexity required to perform the sensing operation, there may be considerable processing required. As will be described hereinbelow, the sensing operation for each axis requires a PID processor for determining information regarding proportionality, performing an integration function and also for performing a differentiation function. This processing involves some relatively complex algorithms that are utilized to define the accelerometer operation and to determine both the magnitude and direction of the acceleration. However, it should be understood that the size of the processing circuitry section 2108 in relation to the accelerometer sensor 2102 can be reduced, and it is anticipated that such circuitry could be included on a similar spherical semiconductor substrate which could be attached to the accelerometer sensor 2102 to decrease the overall size of the device. In any event, it is noted that both the processor substrate 2104 and the accelerometer sensor 2102 are contained as a single encapsulated unit. This is referred to as an accelerometer unit 2210.

Figure 23:
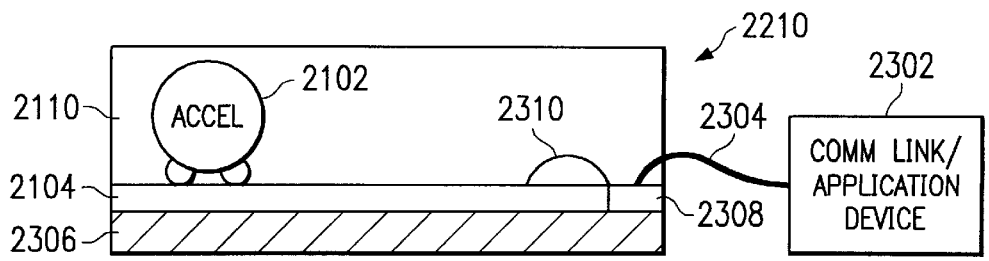
FIG. 23 illustrates a side view of the accelerometer sensor/processor in combination with a communication link/application device.

Referring now to FIG. 23, there is illustrated a side view of the accelerometer unit 2210 utilized in conjunction with a communication link/application interface block 2302. This block 2302 is interfaced with the accelerometer unit 2210 through a flexible interconnection 2304. Typically, this flexible interconnection device 2304 will be interfaced with the processor substrate 2104 at a contact pad and may even have some type of lead frame associated therewith for mounting of the substrate 2104 thereon. This lead frame is represented as an element 2306 of the accelerometer unit 2210 which has a pad 2308 associated therewith that is wire bonded to the processor substrate 2104 through wire bond 2310. The pad 2308 interfaces with the flexible interconnection 2304.

This communication link/application device 2302 can be a separate communication link that can communication information regarding the magnitude and direction of acceleration to an external location or it could be an application device that utilizes the information associated therewith. It may be that the communication/application device 2304 is disposed on a single fixed surface whereas the accelerator unit 2210 is disposed on a separate moving surface and it is a relative movement between the two that is desired, it being understood that this relative movement requires that there be an accelerometer unit associated with the block 2304.

Figure 24:
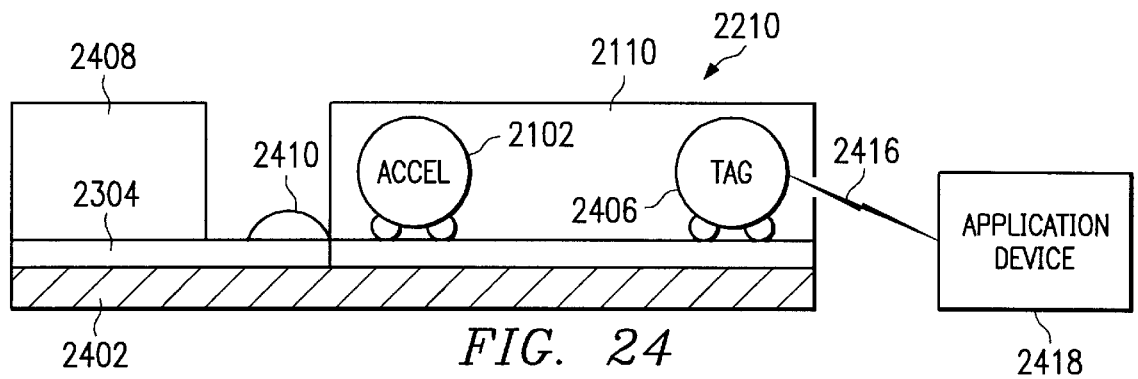
FIG. 24 illustrates a side view of a combined accelerometer sensor, processor and tag.

Referring now to FIG. 24, there is illustrated a side view of the accelerometer unit 2210 disposed on a mounting plate 2402. The accelerometer unit 2210 includes a separate spherical semiconductor device 2406, which is comprised of "tag" unit. This tag unit is a communication device that is operable to allow an interface the processing circuitry 2108 with an external device. This typically comprises some type of RF communication link. This is described in U.S. patent application Ser. No. 09/323,585, filed Jun. 2, 1999, entitled IMPLANTABLE EPICARDIAL ELECTRODE, which is incorporated herein by reference.

In addition to the accelerator unit 2210, a battery 2408 is provided which is interfaced with the processing substrate 2104 and the circuitry 2108 associated therewith through a wire bond 2410, the entire device being encapsulated (not shown). This provides a self-powered stand alone accelerometer that can be disposed in a relatively small area, depending upon the power performance of the processing device. Further, it should be understood that the battery 2408 does not have to be connected to the substrate on the same mounting plate 2402 as the accelerometer unit 2210. It could, in fact, be associated with a separately connected application device block which provides merely a power supply operation, such as the communication link/application device 2302 which is interfaced with the accelerometer unit 2210 through a flexible link 2304, as described hereinabove with reference to FIG. 23.

In the embodiment of FIG. 24, the battery powered accelerometer unit 2210 disposed on mounting plate 2402 is interfaced through a wireless link 2416 between the tag 2406 and an application device 2418. The application device 2418 can perform any application that requires magnitude and direction information from the accelerometer sensor 2102. This wireless connection can be effected over centimeters or even farther, depending upon the power capabilities of the tag 2406 and the receiver sensitivity of the application device 2418. Further, the application device 2418 can transmit information back to the tag 2406 to provide for downloading of control parameters that may be utilized by the processing circuitry 2108 on the processing substrate 2104.

Figure 25:
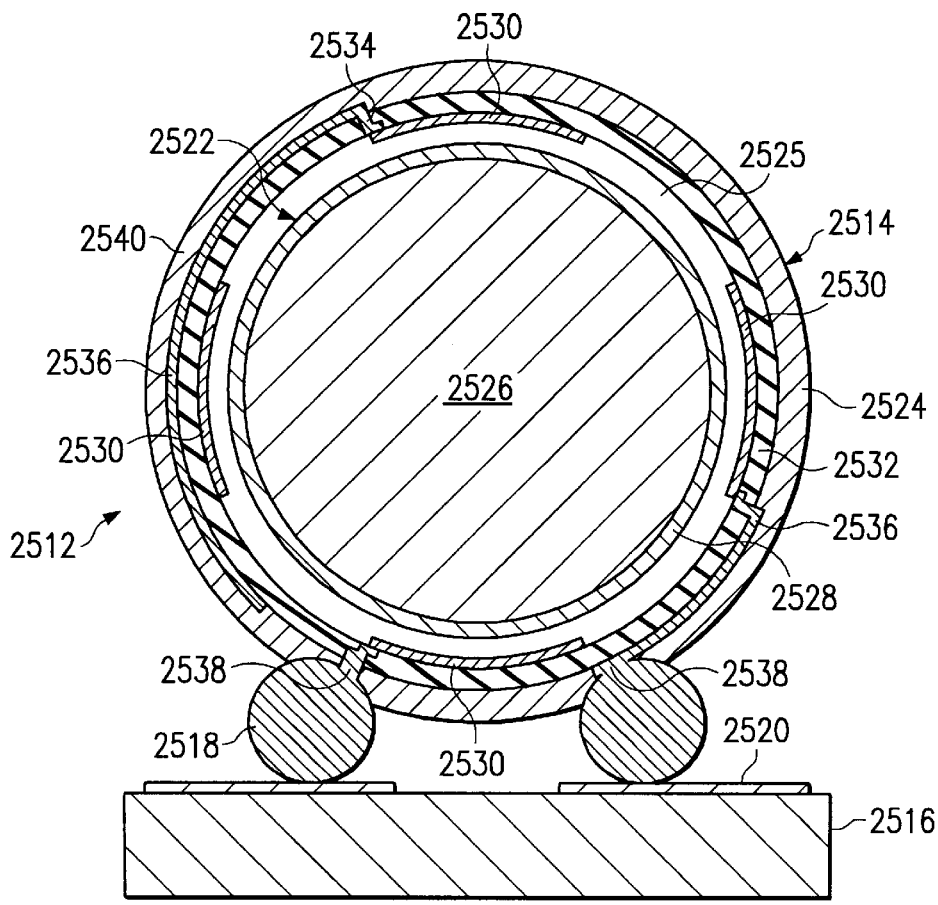
FIG. 25 illustrates a sectional view which schematically depicts the various components of the accelerometer sensor fabricated on a spherical semiconductor substrate.

Referring now to FIG. 25, there is illustrated a motion sensor 2512 provided by a spherical substrate semiconductor for use in the acceleration units 2210. As described below, the motion sensor 2512 may be used for three dimensional measurements such as an inclinometer, an accelerometer, a gyroscope or a magnetometer. The motion sensor 2512 includes a spherical substrate section 2514 which is mounted to a substrate 2516 by connector bumps 2518. The connector bumps 2518 are preferably provided by a solder material. The substrate 2516 has interconnects 2520 for connecting the connector bumps 2518 to other circuitry mounted to the substrate.

The sensor spherical substrate section 2514 includes an inner core 2522 and an outer shell 2524. A gap 2525 exists between the inner core 2522 and outer shell 2524. The inner core 2522 is formed of a solid semiconductor sphere 2526. The semiconductor material used may be silicon, germanium, silicon carbide, or other suitable materials for fabricating solid state circuits therefrom. The surface of the core 2522 has an outer conductive metalization layer 2528 disposed thereon, which is preferably provided by titanium nitride.

The outer shell 2524 has a plurality of electrodes 2530, preferably six, only four of which are shown in FIG. 25. The electrodes 2530 preferably have circular peripheries and are aligned such that one pair of the electrodes 2530 are disposed on opposite sides of the interior of the outer shell 2524 and define axes which are orthogonal to axes defined by respective oppositely disposed pairs of the other electrodes 2530. The electrodes 2530 are formed on the interior surface of a dielectric layer 2532, which is preferably made of silicon dioxide. Vias 2534 extend through the dielectric layer 2532 for passage of interconnects 2536 which connect the electrodes 2530 to respective contacts 2538. The contacts 2538 are connected to respective connector bumps 2518. An outer layer 2540 of the shell 2524 is provided by a photosensitive polymer, which provides mechanical strength. Preferably, EPON SU8 is used as the photosensitive polymer which provides the outer layer 2540.

Figure 26:
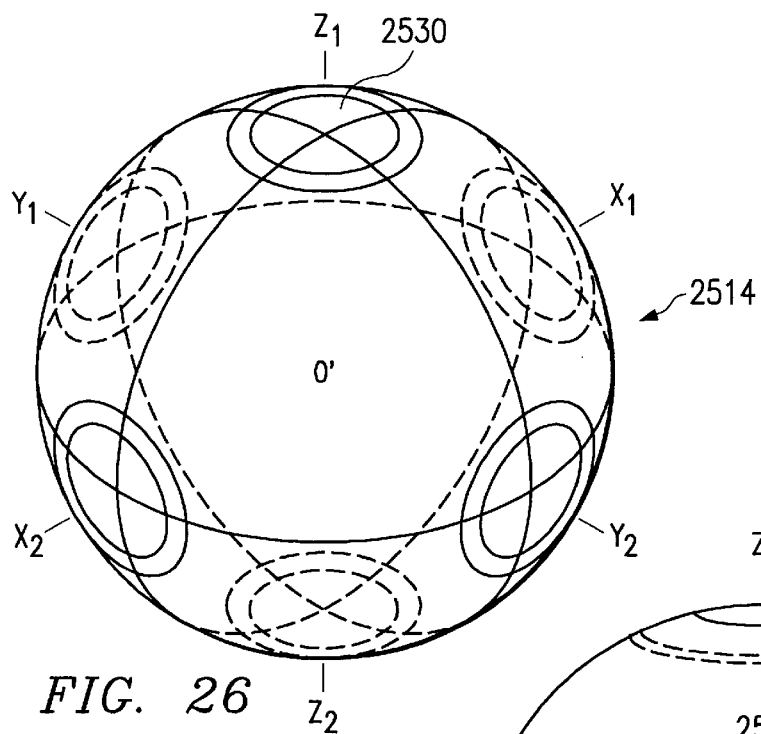
FIG. 26 illustrates a perspective view of the spherical accelerometer sensor.

Referring now to FIG. 26, there is illustrated a perspective view of the sensor spherical substrate 2514 of the motion sensor 2512. The various electrodes 2530 are shown defining various ones of the mutually orthogonally disposed axes X—X, Y—Y and Z—Z of a cartesean coordinate system.

Figure 27:
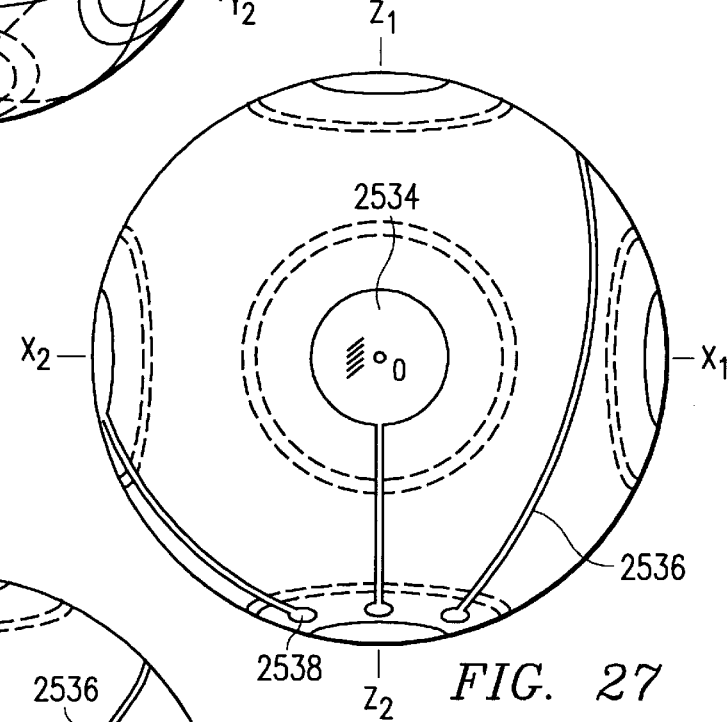
FIG. 27 illustrates a side elevation view of the spherical accelerometer sensor, with an outer layer removed to expose interconnect circuits.

Referring now to FIG. 27, there is illustrated a side elevation view of the motion sensor 2512, with the outer layer 2540 removed to expose the vias 2534, the interconnects 2536 and the contacts 2538.

Figure 28:
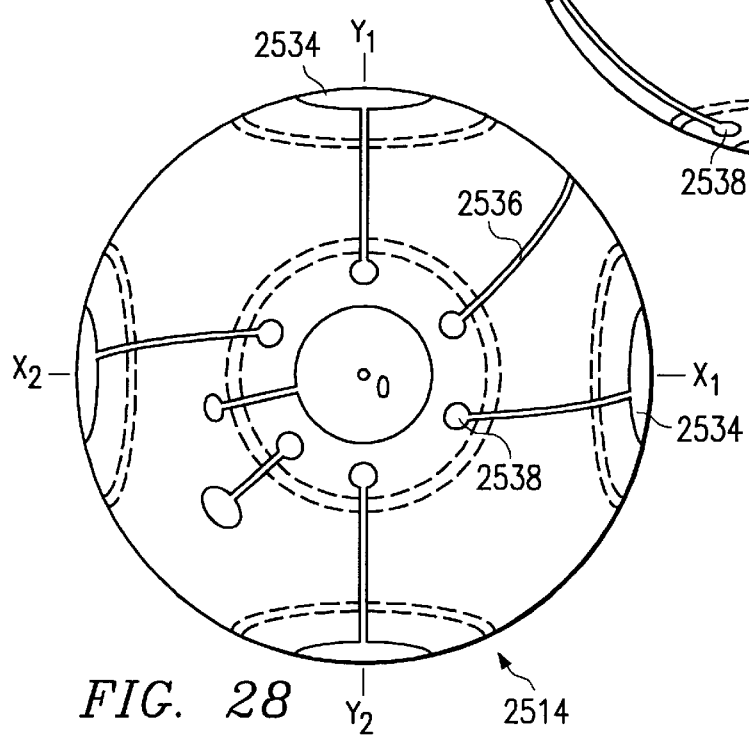
FIG. 28 illustrates a bottom view of a the spherical accelerometer sensor, with the outer layer removed to expose the interconnect circuits.

Referring now to FIG. 28, there is illustrated a bottom view of the sensor spherical substrate 2514, with the outer layer 2540 removed such that the interconnects 2536, the vias 2534 and through the contacts 2538 are disclosed. The bumps 2518 will be secured to the contacts 2538, preferably on the lowermost portion of the sensor spherical substrate 2514.

Figure 29:
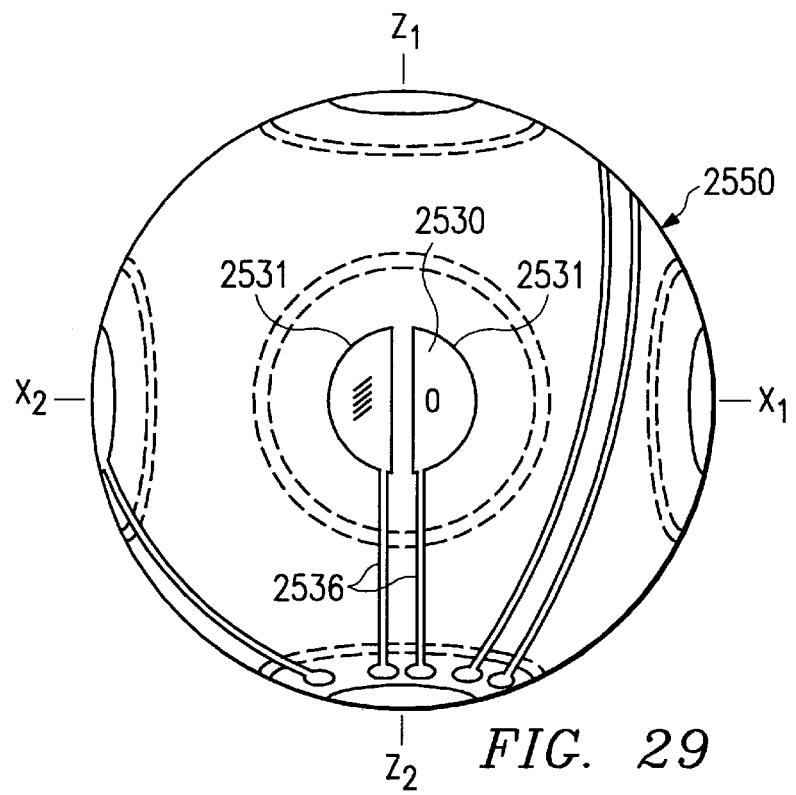
FIG. 29 illustrates a side elevation view of an alternative spherical motion sensor, with the outer layer removed to expose interconnect circuits.
Figure 30:
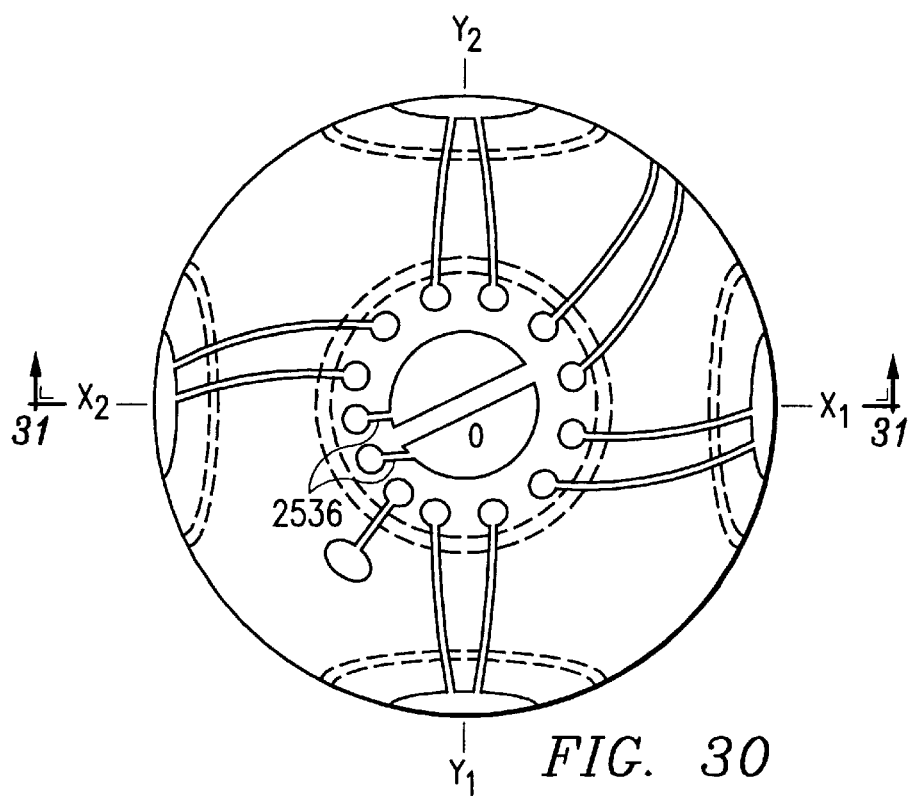
FIG. 30 illustrates a bottom view of the alternative spherical motion sensor, with the outer layer removed to expose the interconnect circuits.

Referring now to FIGS. 29 and 30, there are illustrated a side elevation view and a bottom view of an alternative motion sensor spherical substrate 2950, respectively, with the outer layer 2540 removed. The motion sensor spherical substrate 2950 has electrodes 2530 which are provided such that there are an adjacent pair of electrodes 2531 on each of the locations for the electrodes 2530 of the sensor spherical substrate 2514, which are electrically isolated and contact separate interconnects 2536 to connect separate contacts 2538.

Figure 31:
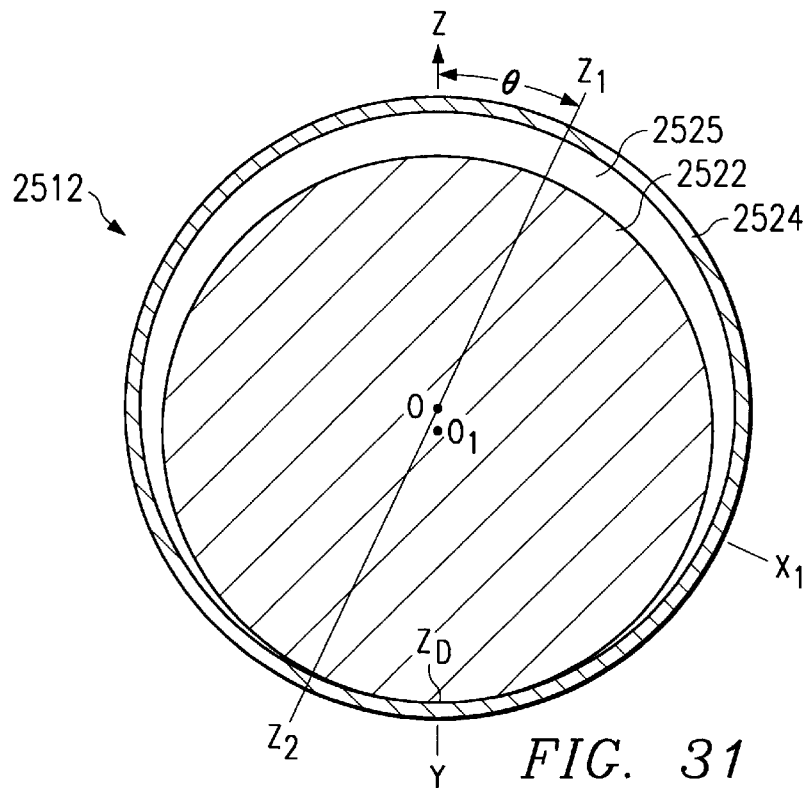
FIG. 31 illustrates a sectional view of the spherical motion sensor, showing the spherical motion sensor being operated in an inclination sensing mode.

Referring now to FIG. 31, there is illustrated a sectional view depicting operation of the motion sensor 2512 in an inclination sensing operating mode. In the inclination sensing operating mode, value for the capacitance between the various ones of the electrodes 2530 and the outer conductive metalization layer 2528 of the inner core 2522 are measured, such that the sizes of the gap 2525 between respective ones of the electrodes 2530 and the outer metalization layer 2528 of the inner core 2522 are determined by detecting the respective values of the capacitances therebetween Thus, as the size of the gap 2525 changes with respect to various ones of electrodes 2530, the respective values for the capacitance therebetween may be determined to determine the respective sizes of the gap 2525 at the respective ones of electrodes 2530, and thereby the relative positioning of the inner core 2522 within the outer shell 2524.

Figure 32:
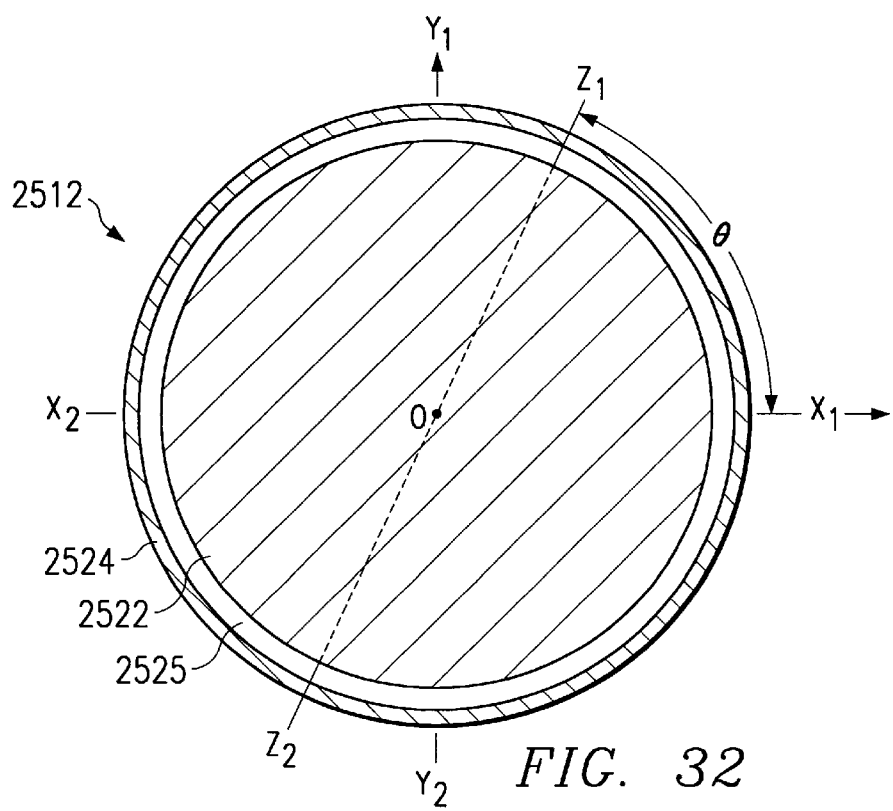
FIG. 32 illustrates a sectional view of the spherical motion sensor, showing the motion sensor being operated in an accelerometer mode.

Referring now to FIG. 32, there is illustrated a side elevational, sectional view of the motion sensor 2512 when being operated in an accelerometer mode. DC voltages are applied to respective ones of electrodes 2530, such that the inner core 2522 is electromagnetically levitated and maintained in a centered position, concentrically disposed within the outer shell 2524. The value for the capacitance between the metalization layer 2528 of the inner core 2522 and the electrodes 2530 is measured using an AC power source and then the detected capacitance value is used as a feedback mechanism to determine the relative positioning of the inner core 2522. The DC voltages are applied to respective ones of the electrodes 2530 in respective values which are determined in accordance to the detected capacitance values for corresponding ones of the electrodes 2530, to concentrically center the inner core 2522 within the outer shell 2524. The values of the voltages applied to the respective electrodes 2530 maintain the inner core in a concentric position within the outer shell 2524 are used to determine the acceleration to which the motion sensor 2512 is exposed, and to determine the direction of the acceleration.

Still referring to FIG. 32, there is illustrated operation of the motion sensor in a gyroscope mode to determine relative angular positioning of the motion sensors 2512 around a central axis of rotation Z1–Z2. Voltages are applied across the electrodes 2530 to levitate the inner core 2522, and also such that the inner core 2522 will spin, and be disposed in a levitated position, concentric with the outer shell 2524. Relative positioning of the axis of rotation of the inner core 2522 relative to the electrodes 2530 is sensed to determine the amount of relative rotation from an initial position between the axes of the outer shell 2524 and the central axis rotation of the inner core 2522. It should be noted that when utilized in the gyroscopic mode, the motion sensor 2512 is useful for determining rotation relative to two mutually orthogonal axes. A second motion sensor 2512 may be used to determine relative rotation of the second motion sensor 2512 relative to a central axis of rotation of an inner core 2522, which is disposed orthogonal to the axes of rotation of the first motion sensor 2512, to fully define the angular positioning of a sensor module in three dimensions.

Referring yet still to FIG. 32, there is also illustrated operation of the motion sensor 2512 in a magnetometer mode of operation. Voltages are applied across the electrodes 2530 such that the inner core 2522 is in a levitated position, concentric with the outer shell 2524. Magnetic charges are then applied to the inner core 2522, such that at least one of the outer conductive metalization layer 2528 and the core 2522 will be polarized with north and south magnetic poles to respond to exteriorly applied magnetic fields, such as the earth's magnetic field. Relative positioning of the inner core 2522 with respect to the outer shell 2524 in three dimension may thus be detected with the electrodes 2530 of the outer shell 2524.

Figure 33:
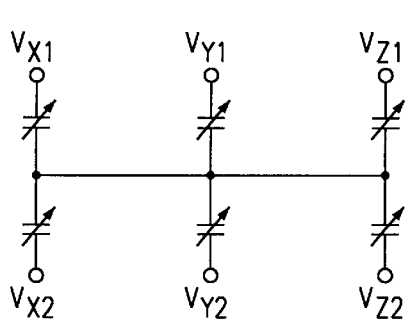
FIG. 33 illustrates a diagrammatic view of a circuit representing the motion sensor.

Referring now to FIG. 33, there is illustrated a circuit which schematically depicts the motion sensor 2512 as an electric circuit. When utilized in either of an inclination mode, an accelerometer mode or a gyroscope mode, the capacitance between the outer metalization layer 2528 of the inner core 2522 and of various ones of the electrodes 2530 is represented by the capacitors in the circuit.

Figure 34:
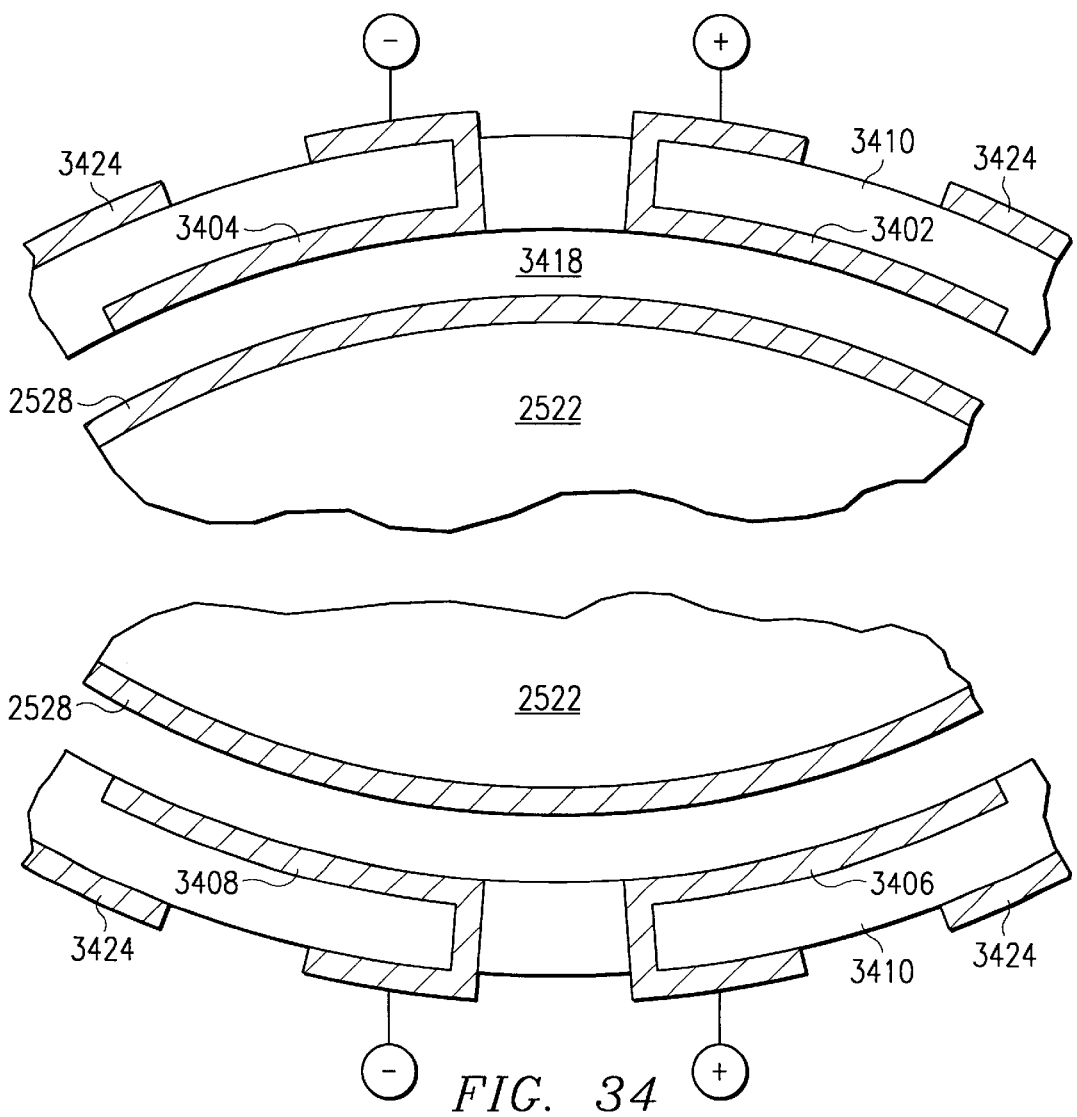
FIG. 34 illustrates a sectional view of two sets of contacts on one axes of the spherical accelerometer sensor.

Referring now to FIG. 34, there is illustrated a sectional view of two of the sensors along a single axis. Each of the contacts is divided into two contacts, a positive contact and a negative contact. There are illustrated for a single axis in the embodiment of the FIG. 34, a top contact comprised of a positive plate 3402 and a negative plate 3404 with the lower contact for that axis having a positive plate 3406 and a negative plate 3408. Each of the plates 3402–3408 extends through an oxide layer 3410 to provide a contact on the upper surface thereof. These contacts allow a connection to the exterior, i.e., they will be connected through some type of conductive run to an external contact for interface with a ball contact. This can then allow interface to another circuit, as described hereinabove.

The inner core 2522 is separated from the outer core by a gap 3418. In the normal state for an accelerometer, this will be electrostatically suspended. This is achieved by providing an AC signal across the two contacts on both sides of a given axis to provide an equal "pulling" force thereto. As long as this is equal, the inner core 2522 will be suspended along the associated axis.

In addition to the contacts for suspending the inner core, there is provided an additional sensing contact 3424 which is basically disposed around the contacts imposing the electrostatic force on the inner core. There is provided one of these contacts 3424 proximate to each of the contacts for each side of each of the three axes. This sensing contact 3424 is for sensing the position of the inner core 2522 along the associated axis. This constitutes the output of the ball, one for each axis, which can then be utilized to adjust the voltages on the associated electrostatic force contacts.

Figure 35:
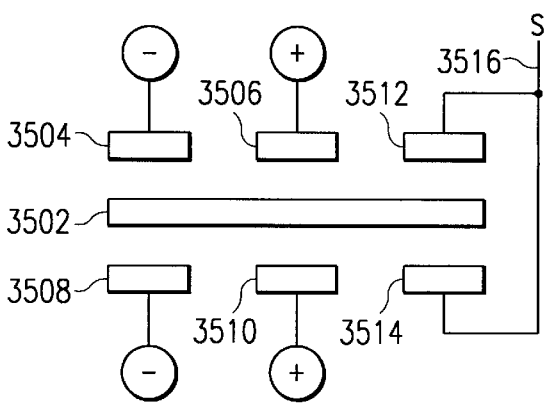
FIG. 35 illustrates a diagrammatic view of the operation of the capacitive configuration for balancing the center core with electrostatic forces.

Referring now to FIG. 35, there is illustrated a schematic diagram of the overall operation for generating the electrostatic force to offset any acceleration. A plate 3502 is illustrated that represents the inner core and the conductive surface thereof, represented by the conductive surface 2528. There are provided on one side of the plate 3502 two plates 3504 and 3506, a negative and positive plate, respectively. Corresponding plates 3508 and 3510 are disposed on the opposite side of the core, these being negative and positive plates, respectively. An AC voltage is applied to both plates on either side of the core to pull the plate 3502 thereto with an equal amount of electrostatic force, thus balancing the core in the presence of zero acceleration. There are provided two additional plates 3512 and 3514 on opposite sides of the plate 3502, these representing the plate 3424 in FIG. 34. This essentially senses the AC signal that is imparted to plate 3502 through the plates 3504–3510. As long as this is balanced, i.e., the capacitance is balanced, then the signal on an output terminal 3516 will be at a defined level. As it varies in level, this will basically sense the position of the plate 3502 relative to the plates 3512 and 3514. Therefore, along one axis, it is only important to insure that the electrostatic forces are equal. If acceleration is imparted to the plate 3502 such that it moves, then the electrostatic force will be adjusted accordingly to again center it, as will be described hereinbelow.

Figure 36:
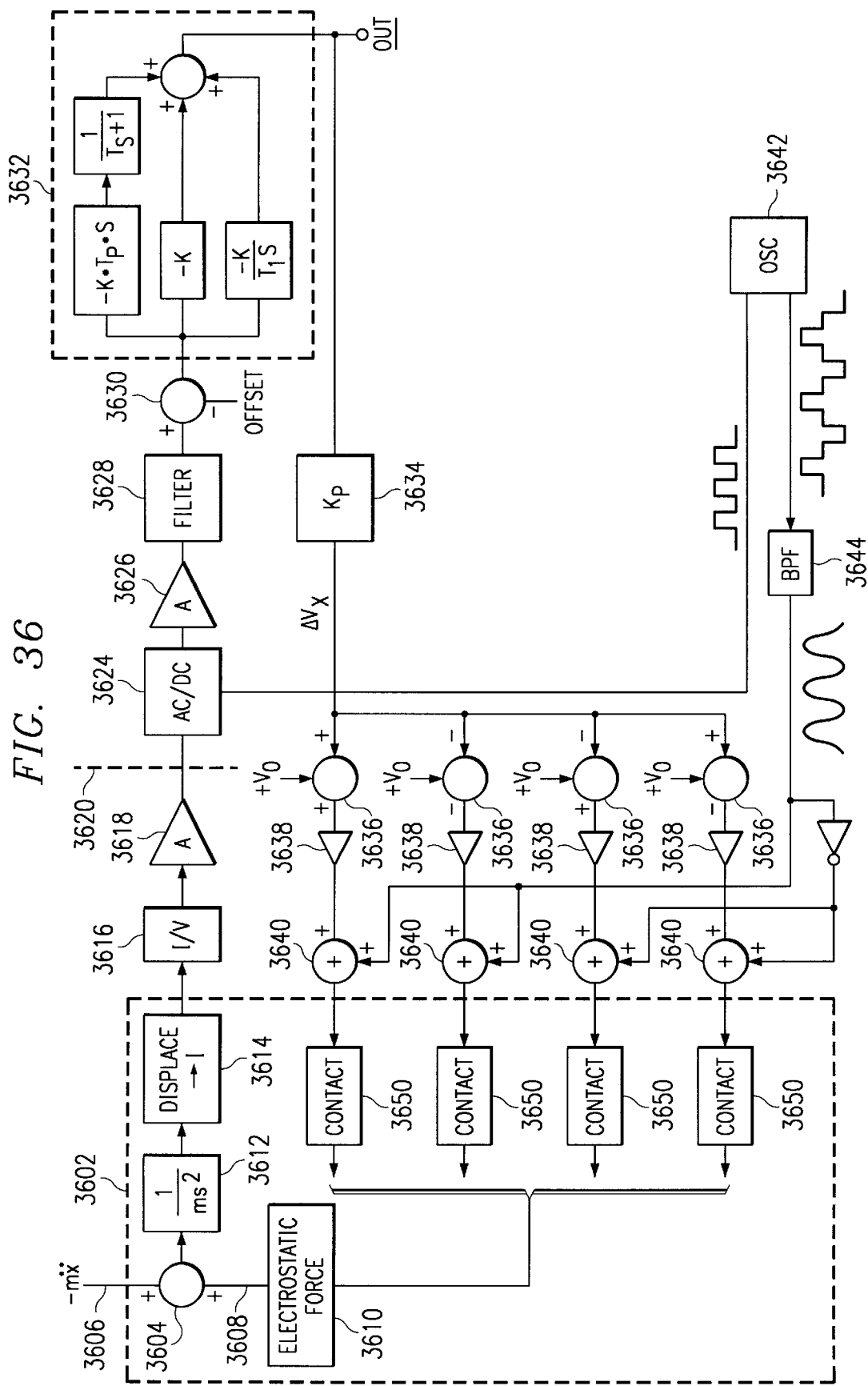
FIG. 36 illustrates a schematic diagram of the overall control operation to measure magnitude and direction of the acceleration.

Referring now to FIG. 36, there is illustrated a schematic diagram of the control system for controlling the operation of the accelerometer sensor 2210, illustrated in FIGS. 34 and 35. In general, there is provided a box 3602 defined by a phantom line. This basically represents the accelerometer sensor. A small sphere 3604 represents the actual inner core which has applied thereto, in diagrammatic representation, has an acceleration −mx imparted thereto on a line 3606 and the electrostatic force imparted thereto on a line 3608, which is provided by a block 3610, this basically representing the force provided by the capacitive plates 3402–3408 in FIG. 34 for a single axis. However, the electrostatic force is imparted for all axes, it being understood that each single axis will require four contacts and a separate processing circuit. The representation in FIG. 36 is for a single axis.

The output of the sphere 3604 provided by the plate 3424 for the associated axis comprises the sensed position of the ball along that axis, which is a displacement. This is represented by a box 3612 representing the displacement $1/ms^2$, which is then represented by a block 3614 which converts displacement to current, this basically being the output line 3516, which is provided through the use of the plate 3424 and the configuration thereof. This output current is an A/C current which is output from the box 3602 and is converted to a voltage through a current-to-voltage converter 3616. This is then amplified in an amplifier 3618.

For the single axis, the output of amplifier 3618 is converted with an AC-to-DC converter 3624 which receives a local oscillator input to operate as an AM demodulator, and then amplified with an amplifier 3626, this being a DC voltage. In general, this is amplitude modulation operation wherein the information is extracted from the amplitude modulated signal. This is processed to the output of amplifier 3626 and is processed through a filter 3628 and then also applied to in an offset circuit 3630. The output of the offset circuit 3630 is input to a PID circuit 3632 which is a process based operation carried out in a DSP. This operation is comprised of a proportionality operation, an integration operation and a differentiation operation. These three operations are required in order to calculate the acceleration along a given axis. The results of this calculation are then multiplied by a constant in a block 3634 to provide a delta voltage therefrom. This delta voltage is the voltage that must be subtracted or added to a reference voltage $V_o$ in order to adjust the electrostatic force. This is input to a plurality of blocks 3636, one for each of the electrostatic force contacts for the associated axis for output through associated signal conditioning circuits 3638 to subtract or add this delta voltage with the voltage $V_o$. The output of each of the signal conditioning circuits 3638 are input to summing blocks 3640 for each of the contacts, which sum the associated output with a 1 MHz signal, the two summing blocks 3640 associated with the upper axis contacts summing with one phase of the I MHz clock and the summing blocks 3640 associated with the lower contacts associated with the inverted form thereof. This 1 MHz signal is derived from an oscillator 3642 that provides a square wave output that drives the AC/DC converter 3624 to provide the amplitude demodulation which basically operates as a local oscillator thereof, which is filtered by a filter 3644 to provide the sine wave output.

The output of each of the summing block 3640 is provided to an associated one of the contacts, represented by contacts 3650. This illustrates only four contacts, two for each side of the axis, for input to the electrostatic force block 3610 to apply an electrostatic force thereto.

In operation, a movement of the center core will result in a current output. This current output is sensed as to its magnitude and the change thereof with respect to time which basically is modulated onto the frequency for those particular contacts. It should be understood that each axis has a separate frequency, such that there is frequency discrimination for each axis. Therefore, the circuit can discriminate which axis the information is coming from, one set of circuitry associated with each axis. By examining only the current at a given frequency, information can be determined as to the displacement of the inner core along the associated axis. This information, as described hereinabove, is processed with the PID block 3632 in order to derive a magnitude therefrom and convert this to a delta voltage that is then translated into an electrostatic force for each of the contacts. This is done in a feedback mode and the loop filter constant for that loop can be adjusted with the various constants to basically result in a nulled value. Also, the output of the PID block 3632 comprises the output for the given axis, which indicates the amount of voltage change that is required to generate the electrostatic force to offset the displacement for the associated acceleration. This basically represents the balance value required for this offset and corresponds to the actual acceleration.

Although described above with the example of neurosurgery, the skilled physician can recognize further application of robotic navigational guidance in both gross and microscopic surgeries of the brain, eye, ear, heart, lung, gastrointestinal tract, urinary tract, joint, and vascular structures.

Other applications will be apparent to the skilled practitioner. Such clinical applications include surgery of the gastrointestinal tract, the brain, vascular surgery in the legs, abdomen or pelvis, lungs, ear, eye, head and neck, joints, shoulders, extremities, and any other medical procedure which could accommodate these small transponder devices.

Although the preferred embodiment has been described in detail, it should be understood that various changes, substitutions and alterations can be made therein without departing from the spirit and scope of the invention as defined by the appended claims.

What is claimed is:

1. A system for sensing relative positions of first and second points, comprising:

first and second substantially spherical transponders, said first transponder disposed at the first point and said second transponder disposed at the second point and each of said first and second transponders including:

communication circuitry for communicating between said first and second transponders, said first transponder transmitting a signal and said second transponder receiving the signal therefrom, distance determination circuitry for determining from the signal received a relative distance between said first and second transponders, and a transmitter for transmitting from said second transponder data relating to the relative distance determined by said second transponder to an external source; and a processing unit for receiving the data transmitted by said second transponder related to the relative distance data and processing that data to determine the relative positions.

2. The system of claim 1, wherein said processing unit includes a display for displaying position data.

3. The system of claim 1, wherein said first and second transponders are attached to fingertips of an examining glove.

4. The system of claim 1, wherein said first transponder is a primary transponder which is attached to a tip of a surgical cutting instrument.

5. The system of claim 4, wherein one or more secondary transponders are attached to a catheter or guidewire which is adapted to be inserted into a body cavity, and said processing unit activates an alarm when said distance between said primary transponder of said cutting instrument and any of said secondary transponders is less than a predetermined value.

6. The system of claim 1, wherein said first and second transponders are used to measure the distance of separation of the pelvic bones.

7. The system of claim 1, wherein said first and second transponders are used to measure cervical dilatation of a cervix during labor and delivery at childbirth by implanting at least said first and second transponders in the cervix.

8. The system of claim 1, used to prevent injury to the ureter during pelvic surgery.

9. The system of claim 1, used to prevent injury to a blood vessel during pelvic surgery.

10. The system of claim 1, used to prevent injury to the biliary tract during surgery.

11. The system of claim 1, wherein said processing unit radiates energy to said first and second transponders at a first frequency to enable operation thereof according to instructions stored internal to each of said first and second transponders.

12. The system of claim 11, wherein said instructions are transmitted from said processing unit.

13. The system of claim 11, wherein in response to said first transponder being energized, said first transponder generates a first omnidirectional signal at a second frequency which is received by said second transponder.

14. The system of claim 13, wherein said first omnidirectional signal is of a frequency different from said first frequency.

15. The system of claim 13, wherein after said second transponder is energized, said second transponder receives said first omnidirectional signal, and in response, generates a second omnidirectional signal at a third frequency which is received by said processing unit.

16. The system of claim 1, wherein a sequence of calibration steps are performed over an approximate operable range prior to normal operation of the system to develop a lookup table of values used in determining said distance.

17. The system of claim 1, wherein said distance is determined by said second transponder and modulated onto a signal which is transmitted from said second transponder to said processing unit.

18. The system of claim 1, wherein each of said transponders comprises three sets of substantially orthogonal coils, each set having a power coil, a transmit coil and a receive coil, and each set for communicating with said processing unit.

19. The system of claim 1, wherein select ones of said transponders contain a stimulus circuit for stimulating tissue during operation of the system.

20. A method for sensing relative positions of first and second points within a patient's body, comprising the steps of:
  disposing within the patient's body a first transponder at the first point and a second transponder at the second point;
  communicating between the first and second transponders, the first transponder transmitting a signal and the second transponder receiving the signal therefrom;
  determining from the signal received a relative distance between the first and second transponders;
  transmitting from the second transponder data relating to the relative distance determined by the second transponder to an external source;
  receiving the data transmitted by the second transponder related to the relative distance data; and
  processing that data to determine the relative positions of the first and second points within the patient's body.

21. The method of claim 20, wherein the step of processing includes the step of displaying position data.

22. The method of claim 20, wherein the step of disposing further comprises the step of attaching the first and second transponders to fingertips of an examining glove.

23. The method of claim 20, wherein the first transponder is a primary transponder which is attached to a tip of a surgical cutting instrument.

24. The method of claim 23, further comprising the steps of:
  attaching one or more secondary transponders to a catheter or guidewire which is inserted into a body cavity in the step of disposing; and
  activating an alarm when the distance between the primary transponder of the cutting instrument and any of the secondary transponders is less than a predetermined value.

25. The method of claim 20, wherein the first and second transponders are used to measure the distance of separation of the pelvic bones.

26. The method of claim 20, wherein the first and second transponders are used to measure cervical dilatation of a cervix during labor and delivery at childbirth by implanting at least the first and second transponders in the cervix.

27. The method of claim 20, further comprising the step of preventing injury to the ureter during pelvic surgery.

28. The method of claim 20, further comprising the step of preventing injury to a blood vessel during pelvic surgery.

29. The method of claim 20, further comprising the step of preventing injury to the biliary tract during surgery.

30. The method of claim 20, further comprising the step of radiating energy to the first and second transponders at a first frequency to enable operation thereof according to instructions stored internal to each of the first and second transponders.

31. The method of claim 30, further comprising the step of transmitting instructions from a processing unit in which the step of processing is performed.

32. The method of claim 30, wherein in response to the first transponder being energized, the first transponder generates a first omnidirectional signal at a second frequency which is received by the second transponder.

33. The method of claim 32, wherein the first omnidirectional signal is of a frequency different from the first frequency.

34. The method of claim 32, wherein after the second transponder is energized, the second transponder receives the first omnidirectional signal, and in response, generates a second omnidirectional signal at a third frequency which is received by the processing unit.

35. The method of claim 20, further comprising the steps of performing a sequence of calibration steps over an approximate operable range prior to normal operation of the system to develop a lookup table of values used in determining the distance.

36. The method of claim 20, wherein the distance is determined by the second transponder and modulated onto a signal which is transmitted from the second transponder to the processing unit in which the step of processing is performed.

37. The method of claim 20, wherein each of the transponders comprises three sets of substantially orthogonal coils, each set having a power coil, a transmit coil and a receive coil, and each set for communicating with a processing unit.

38. The method of claim 20, wherein select ones of the transponders contain a stimulus circuit for stimulating tissue during operation of the system.

39. A method for sensing relative positions of first and second points, comprising the steps of:

disposing a first transponder at the first point and a second transponder at the second point;

radiating energy at a first frequency to the first and second transponders to enable operation thereof;

transmitting a first set of instructions from a processing unit to the first transponder;

transmitting a second set of instructions from the processing unit to the second transponder;

storing the respective instruction sets in the first and second transponders for operation thereof, each according to its own internally stored instructions;

communicating between the first and second transponders, the first transponder transmitting a signal and the second transponder receiving the signal therefrom;

determining from the signal received a relative distance between the first and second transponders;

transmitting data to the processing unit from the second transponder, the data including the relative distance determined by the second transponder;

receiving the data by the processing unit; and processing the data relating to the relative positions between the first and second transponders.

40. The method of claim 39, wherein in response to the first transponder being energized, the first transponder generates a first omnidirectional signal at a second frequency which is received by the second transponder.

41. The method of claim 40, wherein the second frequency is different from the first frequency.

42. The method of claim 40, wherein after the second transponder is energized, the second transponder receives the first omnidirectional signal, and in response, generates a second omnidirectional signal at a third frequency which is received by the processing unit.

43. The method of claim 39, wherein each of the transponders comprises three sets of substantially orthogonal coils, each set having a power coil, a transmit coil and a receive coil, and each set for communicating with a processing unit.

44. The method of claim 39, wherein select ones of the transponders contain a stimulus circuit for stimulating tissue during operation of the method.

45. A method for sensing relative positions of first and second points, comprising the steps of:

disposing a first transponder at the first point and a second transponder at the second point;

physically measuring the distance between the first and second points;

communicating between the first and second transponders, the first transponder transmitting a signal and the second transponder receiving the signal therefrom;

calibrating the signal received to the measured distance between the first and second transponders;

repeating the above-recited sequence of steps at additional separation distances between the transponders over an approximate operable range to develop a lookup table of values in determining separation distance;

beginning normal operation by positioning the transmitters at an unmeasured distance apart within the operable range;

transmitting from the second transponder data relating to the relative distance determined by the second transponder to an processing unit.

receiving the data transmitted by the second transponder related to the relative difference data; and processing that data to determine the relative positions.

46. The method of claim 45, wherein in response to the first transponder being energized, the first transponder generates a first omnidirectional signal which is received by the second transponder.

47. The method of claim 46, wherein the first omnidirectional signal is of a first frequency.

48. The method of claim 46, wherein after the second transponder is energized, the second transponder receives the first omnidirectional signal, and in response, generates a second omnidirectional signal at a second frequency which is received by the processing unit.

49. The method of claim 45, wherein each of the transponders comprises three sets of substantially orthogonal coils, each set having a power coil, a transmit coil and a receive coil, and each set for communicating with the processing unit.

50. The method of claim 45, wherein select ones of the transponders contain a stimulus circuit for stimulating tissue during operation of the method.

* * * * *